(12) United States Patent
Matlock et al.

(10) Patent No.: US 12,357,791 B2
(45) Date of Patent: Jul. 15, 2025

(54) DEFLECTABLE GUIDE FOR MEDICAL INSTRUMENT

(71) Applicant: Acclarent, Inc., Irvine, CA (US)

(72) Inventors: George L. Matlock, Laguna Hills, CA (US); Don Q. Ngo-Chu, Irvine, CA (US); Tuan Pham, Huntington Beach, CA (US); John H. Thinnes, Jr., Mission Viejo, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 17/748,339

(22) Filed: May 19, 2022

(65) Prior Publication Data

US 2022/0339407 A1   Oct. 27, 2022

Related U.S. Application Data

(62) Division of application No. 15/955,232, filed on Apr. 17, 2018, now Pat. No. 11,376,401.
(Continued)

(51) Int. Cl.
*A61M 25/01* (2006.01)
*A61B 1/005* (2006.01)
(Continued)

(52) U.S. Cl.
CPC ....... *A61M 25/0147* (2013.01); *A61B 1/0051* (2013.01); *A61B 1/07* (2013.01);
(Continued)

(58) Field of Classification Search
CPC .......... A61B 2017/00309; A61B 2017/00327; A61B 17/24; A61B 2017/003;
(Continued)

(56) References Cited

U.S. PATENT DOCUMENTS

| 5,656,011 A | 8/1997 | Uihlein et al. |
| 7,833,203 B2 | 11/2010 | Sherman et al. |

(Continued)

FOREIGN PATENT DOCUMENTS

| CN | 101040775 A | 9/2007 |
| CN | 101909532 A | 12/2010 |

(Continued)

OTHER PUBLICATIONS

U.S. Pat. No. 11,376,401.
(Continued)

*Primary Examiner* — Majid Jamialahmadi
(74) *Attorney, Agent, or Firm* — Morgan, Lewis & Bockius LLP

(57) ABSTRACT

An apparatus includes a bod, an actuation assembly, and a guide catheter extending distally from the body. The guide catheter includes an open proximal end, an open distal end, a rigid proximal portion, a bendable distal portion, and a pull wire extending from the bendable distal portion to the rigid proximal portion. A proximal end of the pull wire is coupled with the actuation assembly. The actuation assembly is operable to translate the pull wire relative to the rigid proximal portion to thereby articulate the bendable distal portion.

14 Claims, 32 Drawing Sheets

Related U.S. Application Data

(60) Provisional application No. 62/490,235, filed on Apr. 26, 2017.

(51) Int. Cl.

| | | |
|---|---|---|
| *A61B 1/07* | (2006.01) | |
| *A61B 1/233* | (2006.01) | |
| *A61B 17/00* | (2006.01) | |
| *A61B 17/24* | (2006.01) | |
| *A61M 25/09* | (2006.01) | |
| *A61M 29/02* | (2006.01) | |

(52) U.S. Cl.
CPC .............. *A61B 1/233* (2013.01); *A61B 17/24* (2013.01); *A61M 25/0113* (2013.01); *A61M 25/0136* (2013.01); *A61M 25/09041* (2013.01); *A61M 29/02* (2013.01); *A61B 2017/00309* (2013.01); *A61B 2017/00327* (2013.01); *A61B 2017/00367* (2013.01); *A61B 2217/007* (2013.01)

(58) Field of Classification Search
CPC ........... A61B 2017/00305; A61B 2017/00314; A61B 2017/00318; A61B 2017/00323; A61B 2017/00331; A61M 25/0054; A61M 25/0138; A61M 25/0141; A61M 25/0147
See application file for complete search history.

(56) References Cited

U.S. PATENT DOCUMENTS

| | | | |
|---|---|---|---|
| 8,568,472 | B2 | 10/2013 | Marchand et al. |
| 8,798,721 | B2 | 8/2014 | Dib |
| 8,808,168 | B2 | 8/2014 | Ettwein et al. |
| 9,757,018 | B2 | 9/2017 | Kesten et al. |
| 9,833,293 | B2 | 12/2017 | Wenderow et al. |
| 10,064,555 | B2 | 9/2018 | Kesten et al. |
| 10,123,685 | B2 | 11/2018 | Kermani |
| 10,137,285 | B2 | 11/2018 | Jenkins et al. |
| 11,376,401 | B2 | 7/2022 | Matlock et al. |
| 2006/0135961 | A1* | 6/2006 | Rosenman ......... A61B 17/0057 604/95.04 |
| 2008/0183128 | A1 | 7/2008 | Morriss et al. |
| 2010/0030031 | A1 | 2/2010 | Goldfarb et al. |
| 2011/0004057 | A1 | 1/2011 | Goldfarb et al. |
| 2011/0251519 | A1* | 10/2011 | Romoscanu ...... A61M 25/0053 600/585 |
| 2012/0071856 | A1 | 3/2012 | Goldfarb et al. |
| 2012/0078118 | A1 | 3/2012 | Jenkins et al. |
| 2014/0074141 | A1 | 3/2014 | Johnson et al. |
| 2014/0135685 | A1* | 5/2014 | Kabe ....................... A61F 2/246 604/95.04 |
| 2014/0275804 | A1* | 9/2014 | Kesten ....................... A61F 5/08 600/249 |
| 2016/0067453 | A1 | 3/2016 | Braithwaite et al. |
| 2016/0302820 | A1* | 10/2016 | Hibner ........... A61B 17/320016 |
| 2016/0346513 | A1 | 12/2016 | Swaney et al. |
| 2017/0080186 | A1 | 3/2017 | Salahich et al. |
| 2018/0001058 | A1 | 1/2018 | Schlesinger |
| 2018/0132875 | A1 | 5/2018 | Singh et al. |
| 2018/0296798 | A1* | 10/2018 | Lepak ............... A61M 25/0136 |
| 2019/0030287 | A1* | 1/2019 | Just .......................... A61B 8/12 |
| 2019/0307420 | A1 | 10/2019 | Minas et al. |

FOREIGN PATENT DOCUMENTS

| | | |
|---|---|---|
| CN | 103068297 A | 4/2013 |
| CN | 204092774 U | 1/2015 |
| CN | 104602750 A | 5/2015 |
| JP | 2001-522270 A | 11/2001 |
| JP | 2013-176465 A | 9/2013 |
| JP | 2016-536090 A | 11/2016 |
| JP | 2017-500083 A | 1/2017 |
| KR | 2008-0087111 A | 9/2008 |
| WO | WO 2003/037416 A1 | 5/2003 |
| WO | WO 2008/144401 A1 | 11/2008 |
| WO | WO 2013/129635 A1 | 7/2015 |
| WO | WO 2016/160805 A1 | 10/2016 |

OTHER PUBLICATIONS

Chinese Office Action and Search Reported dated May 28, 2021, for Application No. 201810383274.1, 16 pages.
Chinese Office Action dated Feb. 28, 2022, for Application No. 201810383274.1, 9 pages.
Chinese Office Action dated May 26, 2022, for Application No. 201810383274.1, 4 pages.
Extended European Search Report dated Jul. 6, 2018, for Application No. 18169165.0, 10 pages.
Japanese Notification of Reasons for Refusal dated Mar. 29, 2022, for Application No. 2018-083645, 3 pages.
Japanese Decision of Refusal dated Oct. 18, 2022, for Application No. 2018-083645, 3 pages.
U.S. Appl. No. 62/490,235, entitled "Deflectable Guide for Medical Instrument," filed Apr. 26, 2017.

* cited by examiner

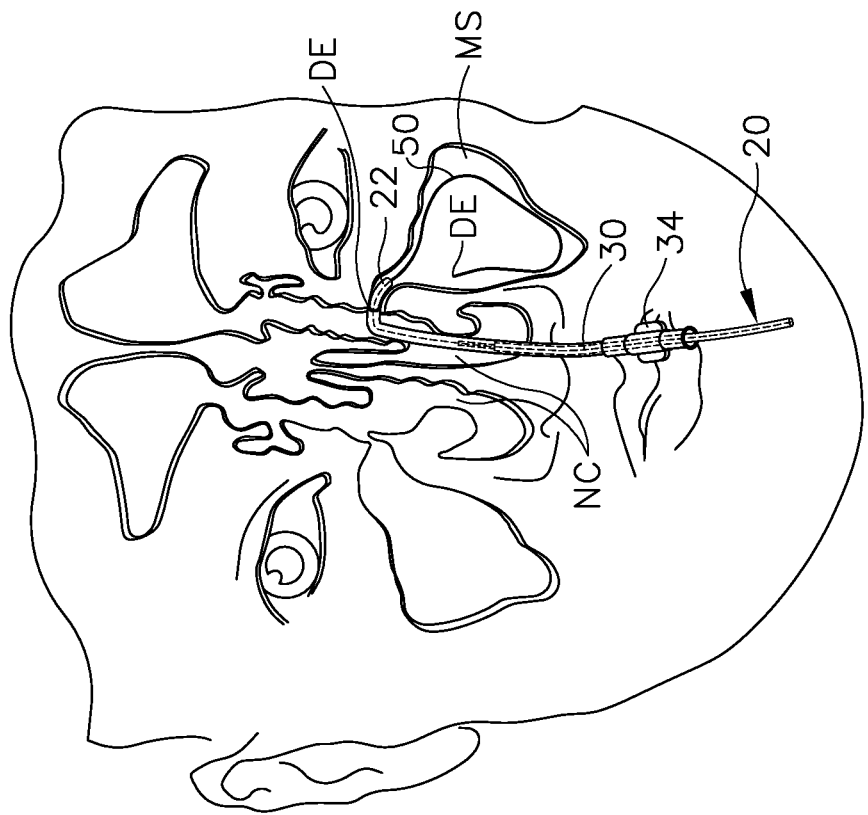
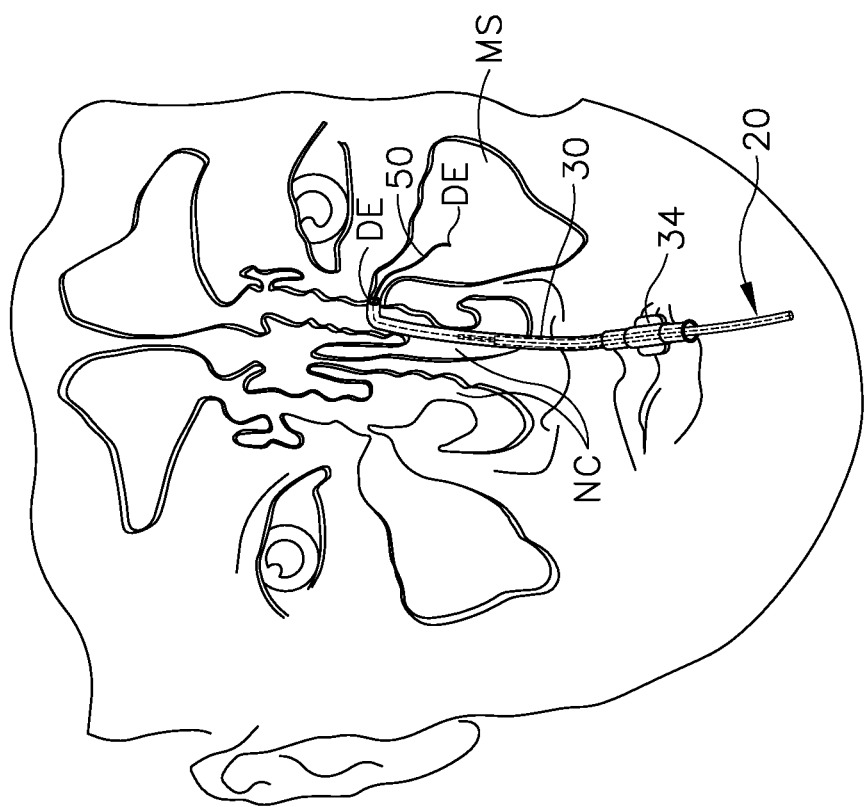

DEFLECTABLE GUIDE FOR MEDICAL INSTRUMENT

PRIORITY

This application is a continuation of U.S. application Ser. No. 15/955,232, filed Apr. 17, 2018, and issued as U.S. Pat. No. 11,376,401, on Jul. 5, 2022, entitled "Deflectable Guide for Medical Instrument."

This application claims priority to U.S. Provisional Patent App. No. 62/490,235, entitled "Deflectable Guide for Medical Instrument," filed Apr. 26, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and guide catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty System by Acclarent, Inc. of Irvine, California.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry® Sinus Illumination System by Acclarent, Inc. of Irvine, California.

It may be desirable to provide easily controlled placement of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus;

FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus;

Figure 1:
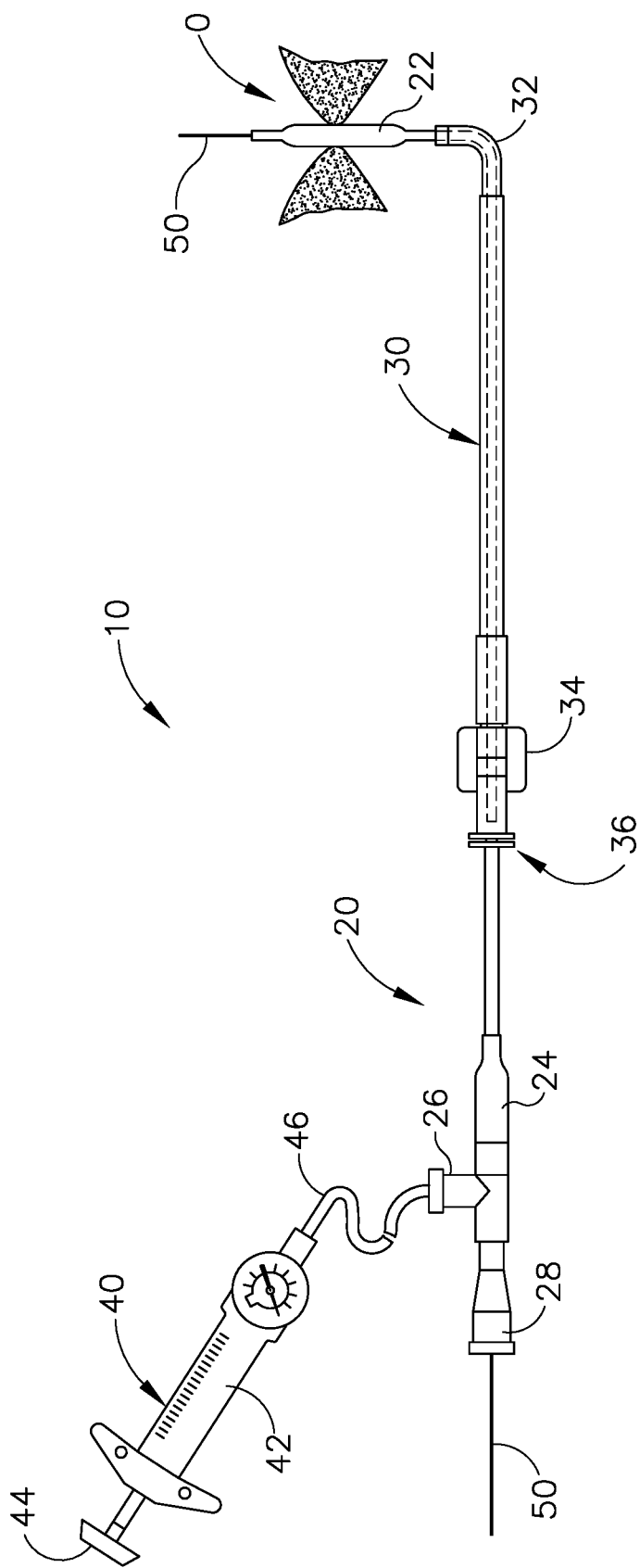
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty System by Acclarent, Inc. of Irvine, California.

Figure 2A:
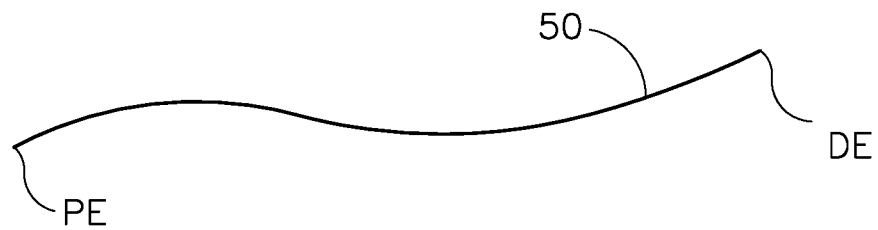
FIG. 2A depicts a side elevational view of an exemplary illuminating guidewire of the dilation catheter system of FIG. 1.
Figure 2B:
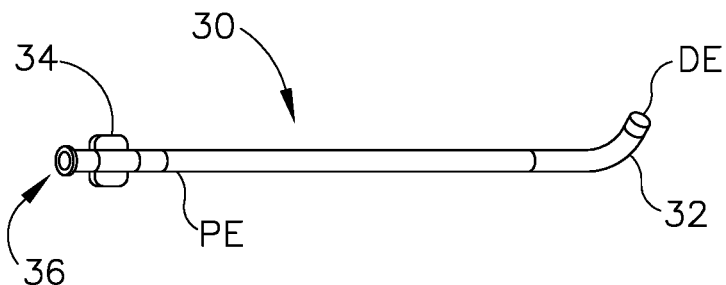
FIG. 2B depicts a side elevational view of an exemplary guide catheter of the dilation catheter system of FIG. 1.
Figure 2C:
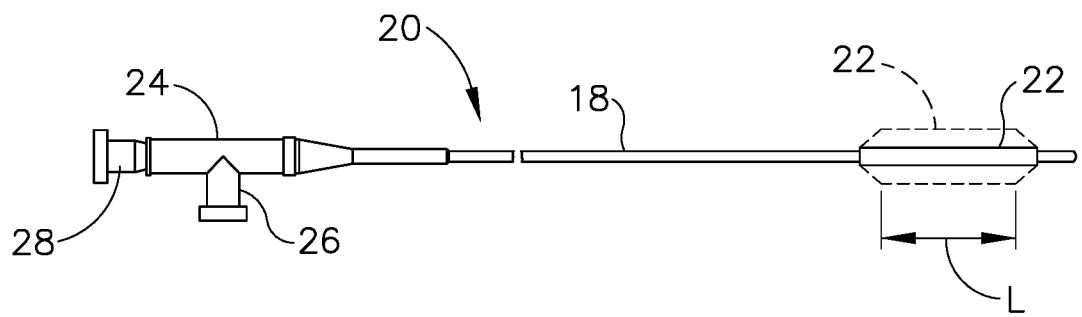
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra® Sinus Balloon Catheter by Acclarent, Inc. of Irvine, California. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex® Sinus Guide Catheter by Acclarent, Inc. of Irvine, California. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

Figure 3:
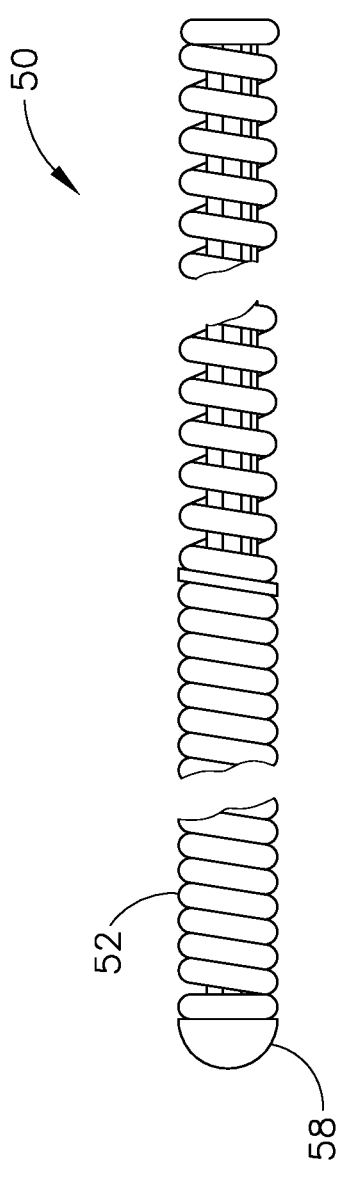
FIG. 3 depicts a detailed side elevational view of the illuminating guide wire of FIG. 2A.
Figure 4:
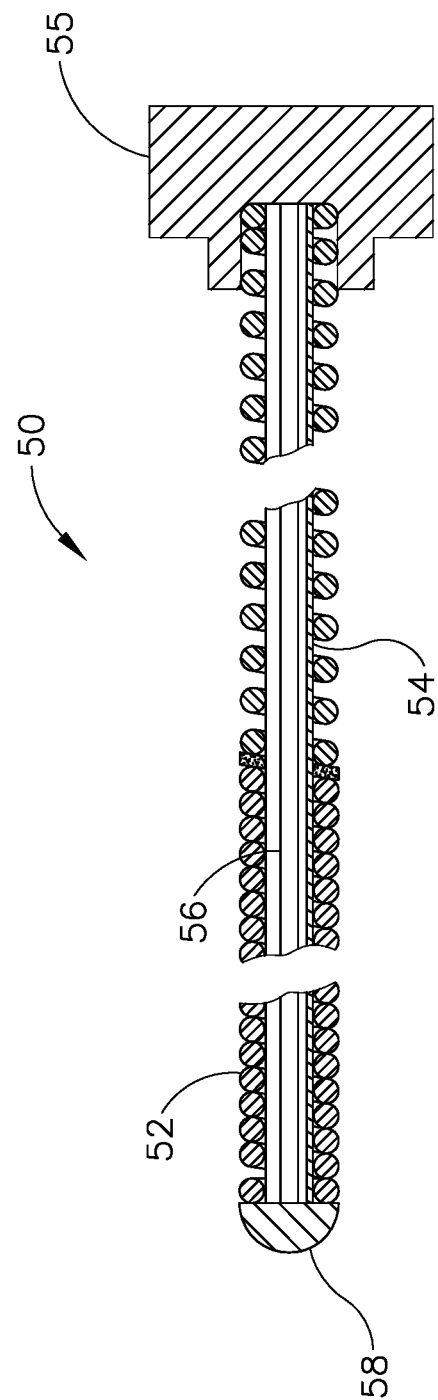
FIG. 4 depicts a detailed side cross-sectional view of the illuminating guidewire of FIG. 2A.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry® Sinus Illumination System by Acclarent, Inc. of Irvine, California. Other suitable forms that guidewire (50) may take will be apparent to those of ordinary skill in the art in view of the teachings herein.

II. Overview of Exemplary Endoscope

Figure 5:
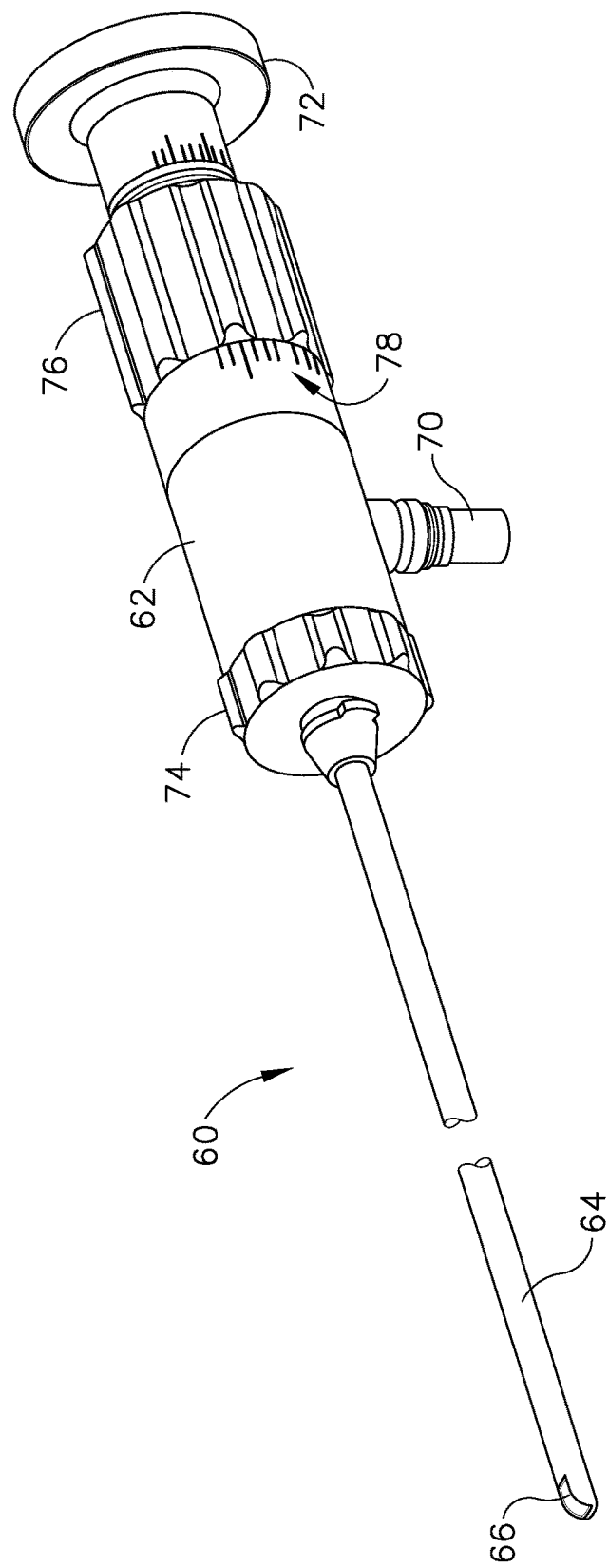
FIG. 5 depicts a perspective view of an exemplary endoscope suitable for use with the dilation catheter system of FIG. 1.
Figure 6:
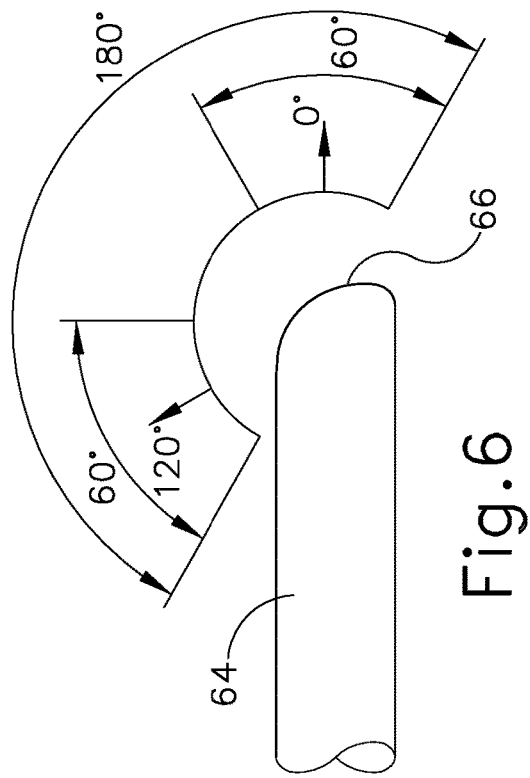
FIG. 6 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. Other suitable forms that endoscope (60) may take will be apparent to those of ordinary skill in the art in view of the teachings herein

III. Exemplary Method for Dilating the Ostium of a Maxillary Sinus

FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
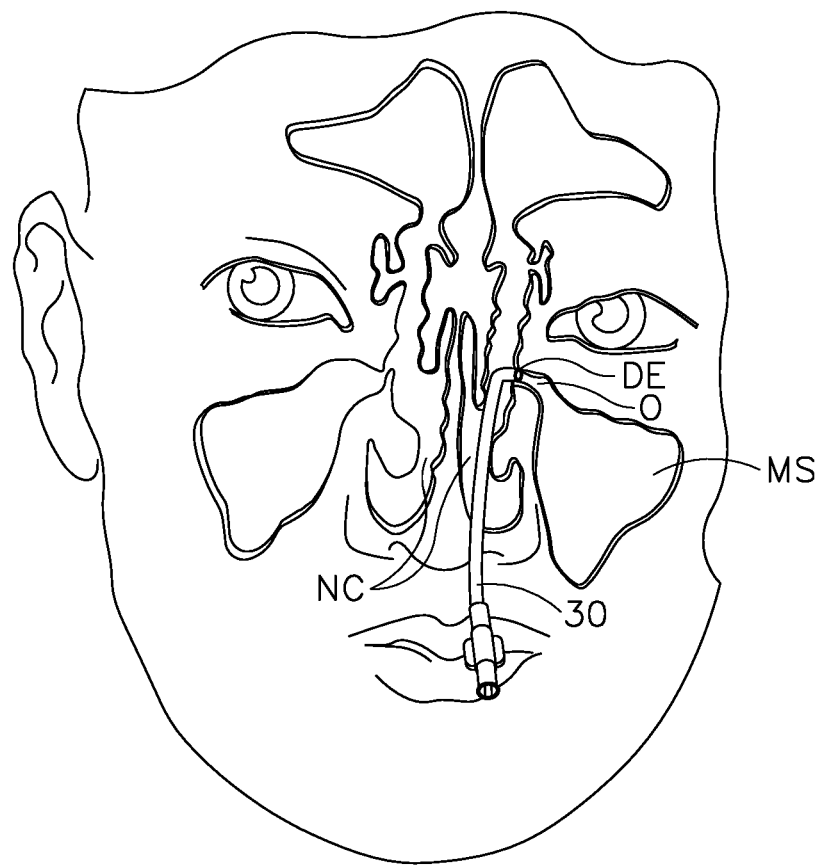
FIG. 7A depicts a front view of the guide catheter of FIG. 2B positioned adjacent an ostium of the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7E:
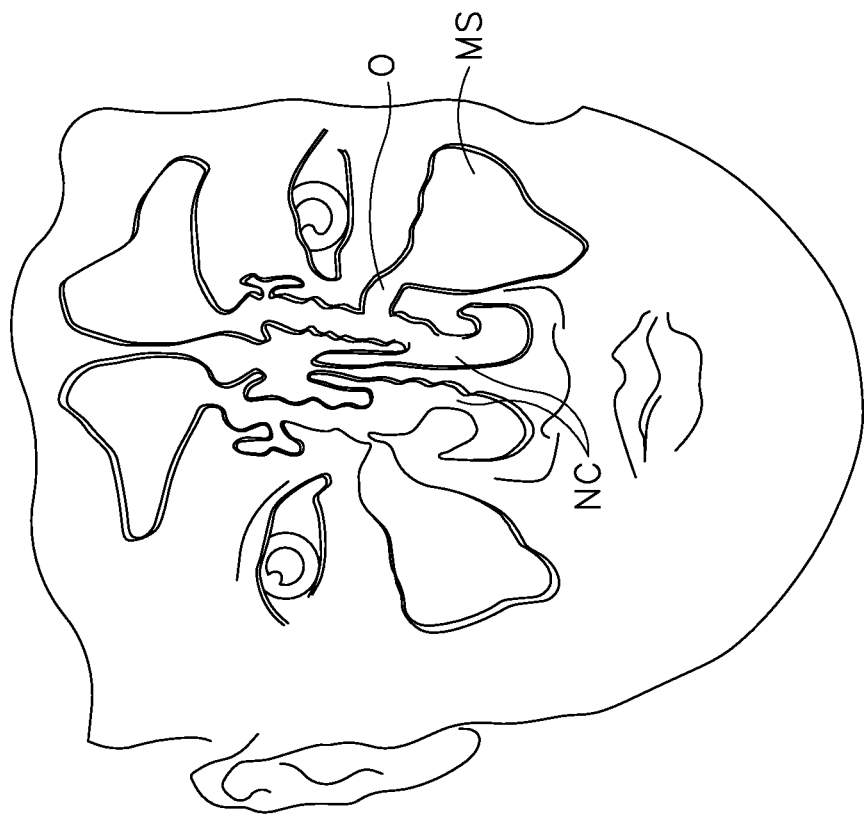
FIG. 7E depicts a front view of an ostium of the maxillary sinus, with the ostium having been enlarged by inflation of the balloon of FIG. 7D.
Figure 7D:
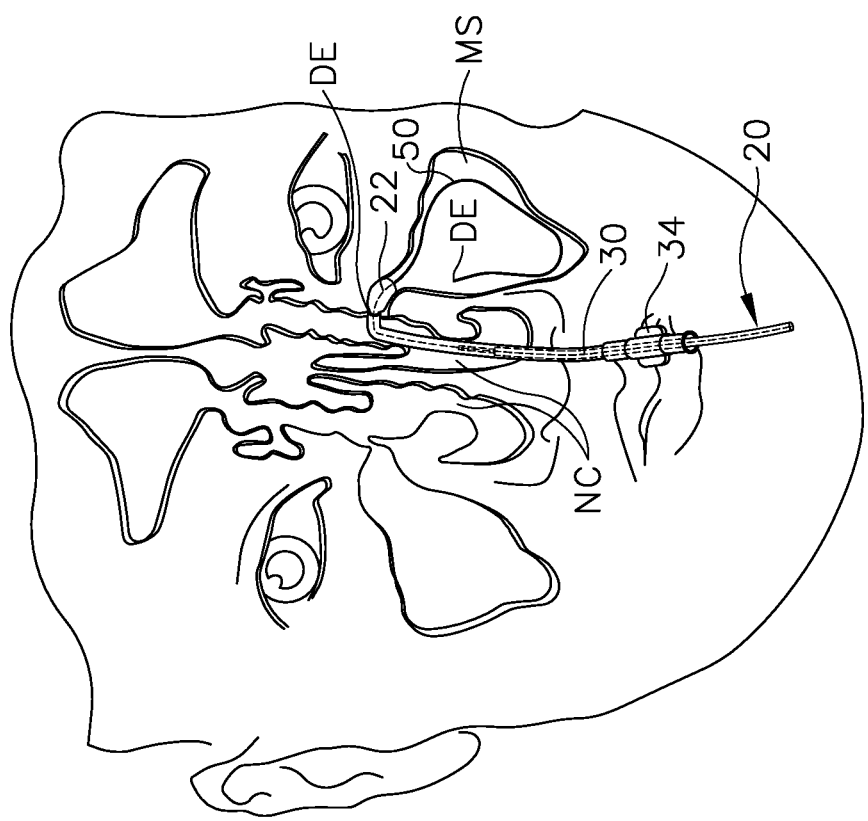
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.
Figure 8:
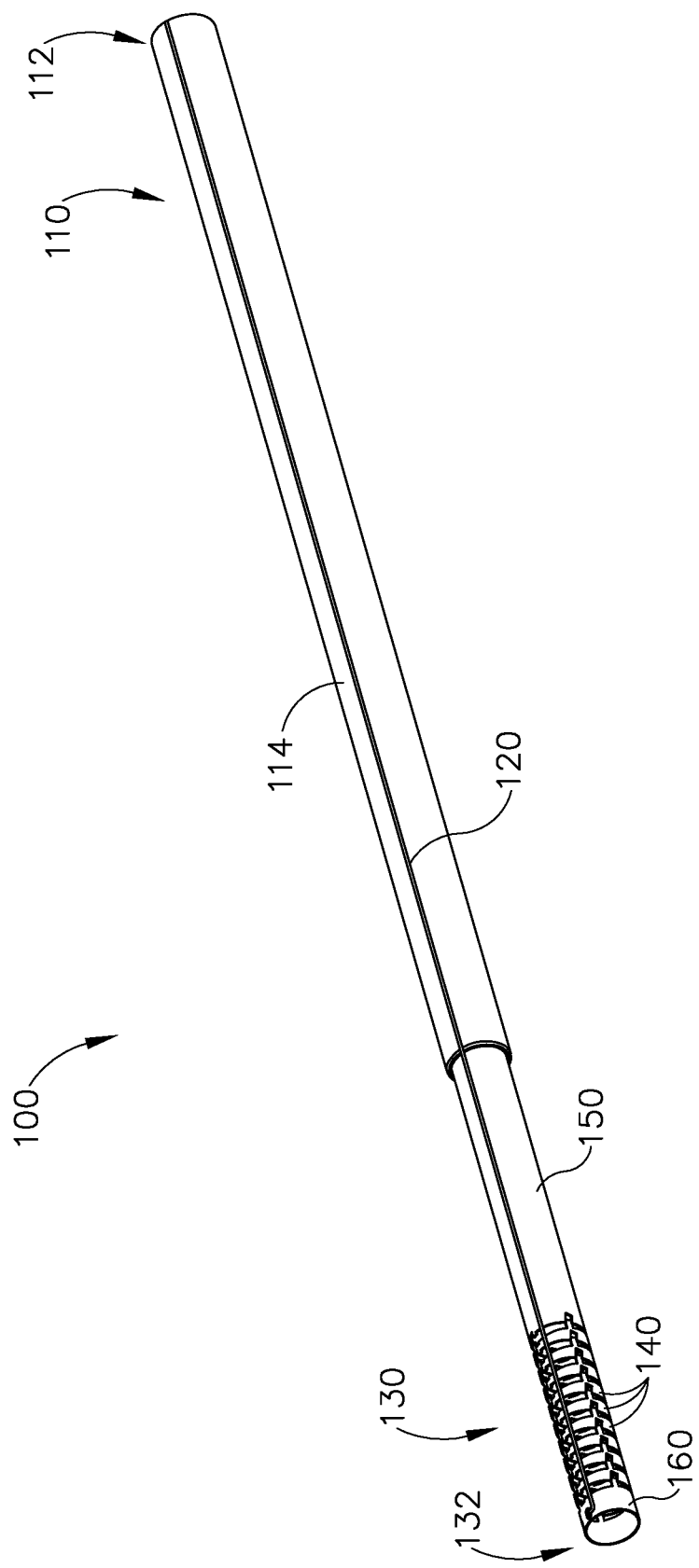
FIG. 8 depicts a perspective view of an alternative exemplary guide catheter.
Figure 9:
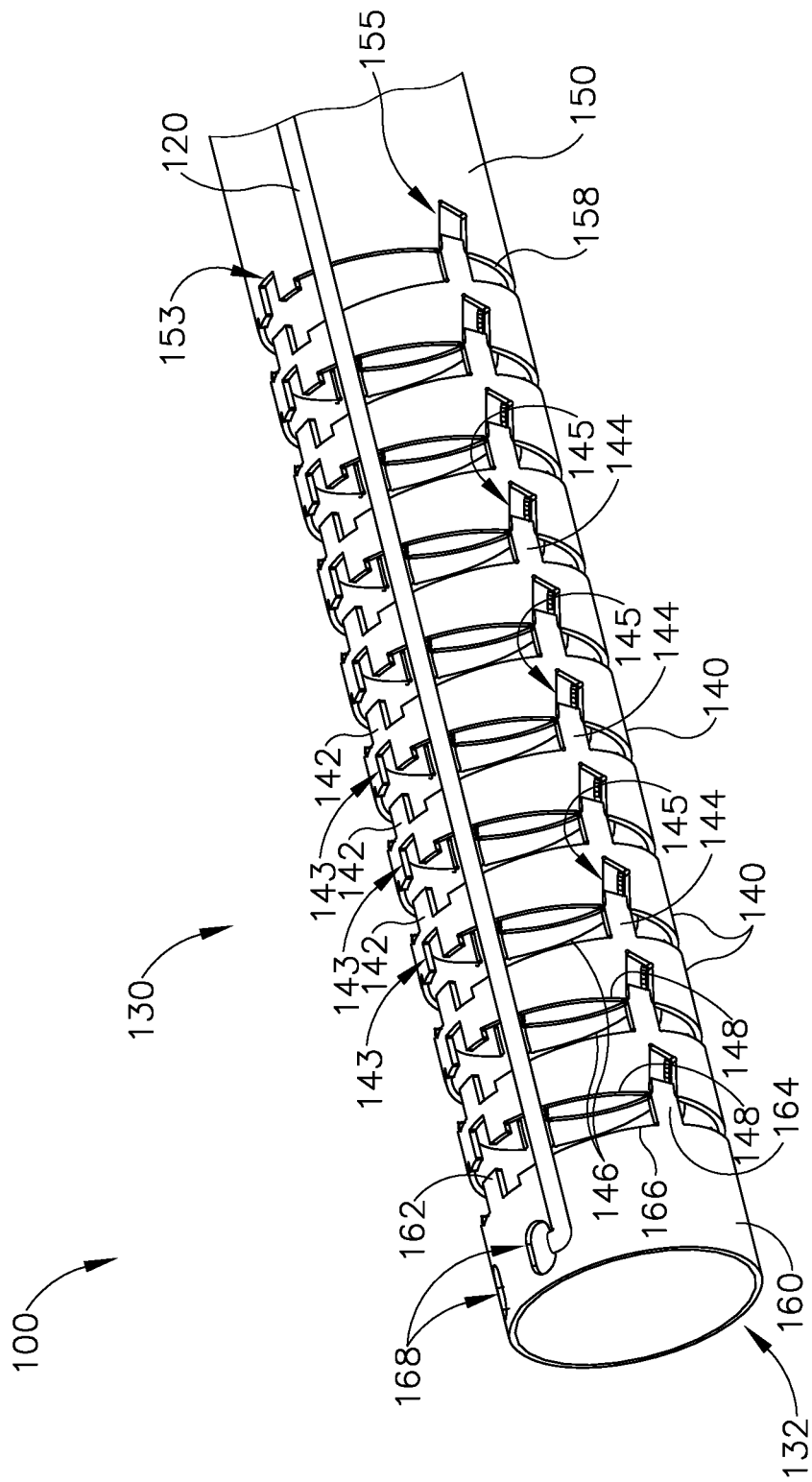
FIG. 9 depicts a perspective view of the distal end of the guide catheter of FIG. 8.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," Published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Irvine, California. Another example of an irrigation catheter that may be fed through guide catheter (30) to reach the irrigation site after removal of dilation catheter (20) is the Relieva Ultirra® Sinus Irrigation Catheter by Acclarent, Inc. of Irvine, California. Of course, irrigation may be provided in the absence of a dilation procedure; and a dilation procedure may be completed without also including irrigation.

IV. Exemplary Alternative Guide Catheter with Distal Articulation Assembly

As described above, guide catheter (30) includes a bent distal portion (32) at its distal end (DE). Bent distal portion (32) may be configured to access a particular sinus ostium (O) when inserted transnasally and advanced through the nasal cavity (NC) of a patient. Additionally, bent distal portion (32) of guide catheter (30) may require sufficient rigidity such that guide catheter (30) maintains its longitudinal profile when an operator applies force to the distal end (DE) during insertion and advancement of guide catheter (30). Because guide catheter (30) includes a predetermined bent distal portion (32), an operator may be required to use multiple guide catheters (30) having various bent distal portions (32) during a procedure if an operator desires to access various nasal/sinus cavities within a patient. Currently, an operator may access various desired locations within the nasal cavity (NC) by removing a first guide catheter (30) with a first bent distal portion (32), and replacing the first guide catheter (30) with a second guide catheter having a different bent distal portion suitable for access of a particular location within the nasal cavity (NC).

Therefore, it may be desirable to articulate/bend the distal end of a guide catheter from the longitudinal axis defined by the rest of the guide catheter while also maintaining suitable rigidity in order to access various locations within the nasal cavity (NC) without having the manually change guide catheters (30). It may further be desirable to selectively articulate/bend the distal end of a guide catheter during a dilation procedure at various angles while the distal end of the guide catheter is adjacent to a targeted area. In other words, it may be desirable to bend the distal end of the guide catheter while the guide catheter is within an anatomical passageway of a patient. Selective articulation/bending of the distal end of a guide catheter during a procedure may provide better steering capabilities within a nasal cavity of a patient, allowing an operator to more easily position a dilator within a targeted area. For instance, the operator may initially insert the catheter into the patient's nasal cavity while the catheter is in a straight configuration; then bend the distal end of the catheter after the catheter is positioned in the patient's nasal cavity. The bend angle may be selectively customized to facilitate access to a drainage passageway associated with a particular paranasal sinus cavity. For instance, the operator may selectively adjust the bend angle to access a drainage passageway associated with a frontal sinus, a maxillary sinus, a sphenoid sinus, or an ethmoid sinus. The following is an exemplary guide catheter coupled with various suitable handles having distal articulation/bending features configured to deflect the distal end of a guide catheter while remaining sufficiently rigid such that the bent distal end resists unwanted bending during suitable use of the guide catheter. Additionally, handles may articulate/bend guide catheter while guide catheter is located adjacent to a targeted area within a patient.

FIGS. 8-11 show an exemplary guide catheter (100) with an articulating distal portion (130) that may be attached to various guide catheter handles (200, 300, 400) such that guide catheter (100) and the selected guide catheter handle (200, 300, 400) may be readily incorporated into dilation catheter system (10) as a replacement of guide catheter (30). Guide catheter (100) includes articulating distal portion (130), a proximal portion (110) extending into articulating distal portion (130), and a pair of pull wires (120) extending from articulating distal portion (130) toward open proximal end (112). As will be described in greater detail below, pull wire (120) is coupled near a distal end of articulating distal portion (130) while pull wire (120) is configured to translate relative to proximal portion (110) in order to selectively articulate/bend articulating distal portion (130).

Proximal portion (110) includes a rigid shaft (114) proximally terminating into an open proximal end (112). Articulating distal portion (130) includes a rigid portion (150) connected to a distal end of rigid shaft (114), a linear array of articulating ribs (140) extending distally from rigid portion (150), and a distal rib (160) extending from the most distal linear array of articulating ribs (140). While the current example has rigid shaft (114) coupled to a rigid portion (150) of articulating distal portion (130), it should be understood that these may be unitarily attached, or divided into more sections. Distal rib (160) includes an open distal end (132). A lumen extends from open proximal end (112) all the way to open distal end (132). The lumen is configured to slidably receive dilation catheter (20), such that guide catheter (100) may receive dilation catheter (20) at open proximal end (112), and such that guide catheter (100) may guide dilator (220) out through open distal end (132).

Figure 10:
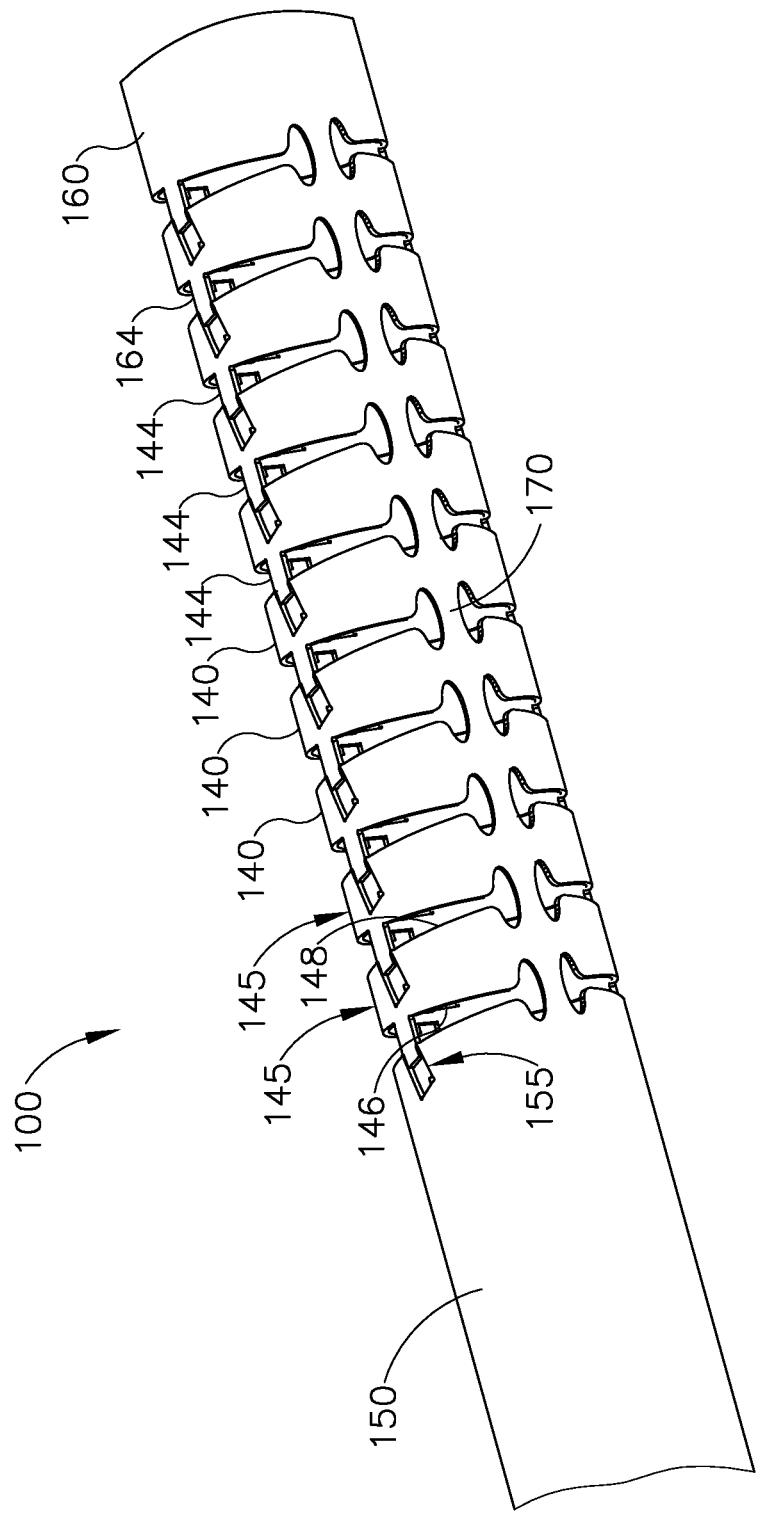
FIG. 10 depicts another perspective view of the distal end of the guide catheter of FIG. 8.
Figure 11:
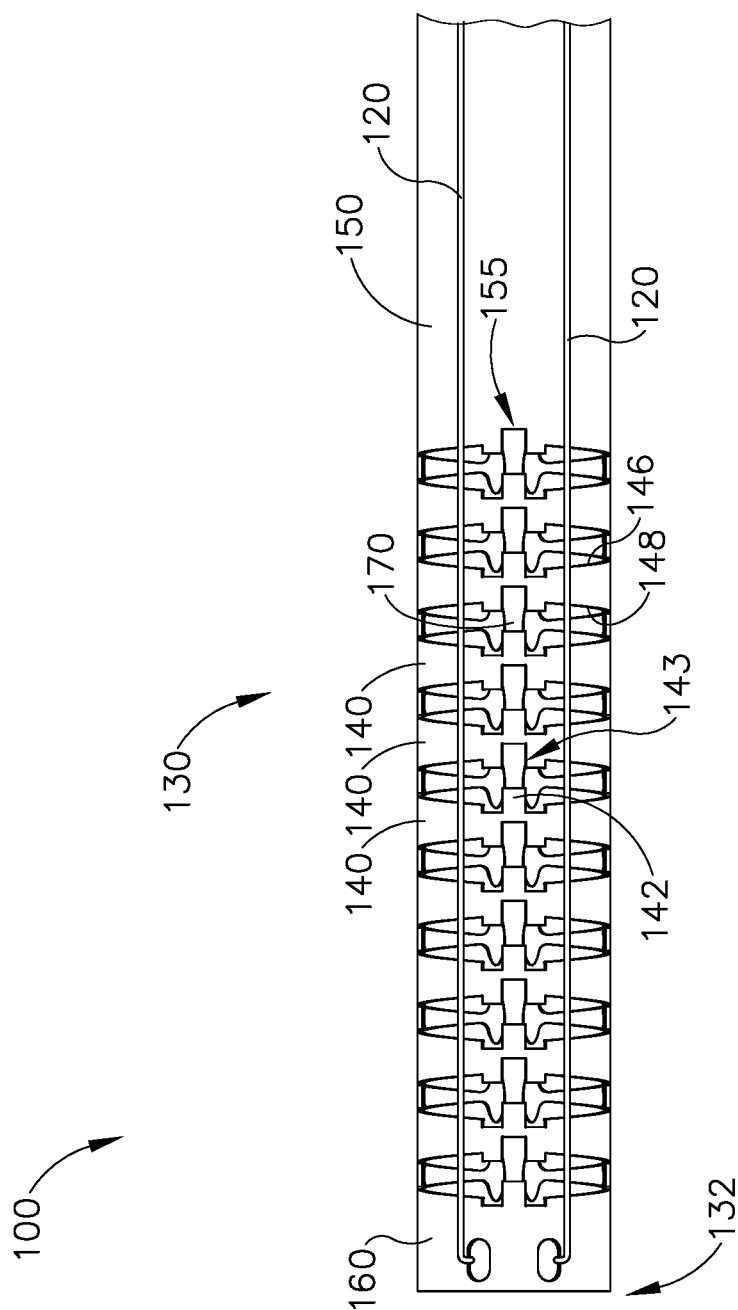
FIG. 11 depicts a top plan view of the distal end of the guide catheter of FIG. 8.

As best seen in FIG. 10, a resilient spine (170) extends along the bottom of articulating distal portion (130) to connect rigid portion (150), linear array of articulating ribs (140), and distal rib (160). In other words, resilient spine (170) acts as a resilient living hinge to connect rigid portion (150), liner array of articulating ribs (140), and distal rib (160). As will be described in greater detail below, resilient spine (170) accommodates articulation of distal rib (160) and articulating ribs (140) relative to rigid portion (150) in response to translation of pull wire (120).

The distal end of rigid portion (150) includes a distal surface (158) and defines a top linear distally presented pocket (153) and a pair of side arched distally presented pockets (155). Each articulating rib (140) includes a top linear proximally presented protrusion (142), a pair of side arched proximally presented protrusions (144), a proximal angled surface (146), and a distal angled surface (148). Additionally, each articulating rib (140) defines a top linear distally presented pocket (143) and a pair of side arched distally presented pockets (145). Distal rib (160) includes a top linear proximally presented protrusion (162), a pair of side arched proximally presented protrusions, and a proximal surface (166). Additionally, distal rib (160) also defines a pair of pull wire coupling holes (168). A distal end of pull wire (120) may couple with distal rib (160) via pull wire coupling holes (168).

Proximally presented protrusions (162, 164) of distal rib (160) are configured to slide within the distally presented pockets (143, 145) of the distal most articulating rib (140), respectively, during articulation of articulating distal portion (130). Similarly, proximally presented protrusions (142, 144) of the proximal most articulating rib (140) are configured to slide within distally presented pockets (153, 155) of rigid portion (150), respectively, during articulation of articulating distal portion (130). Proximally presented protrusions (142, 144) of each articulating rib (140) between the most distal and most proximal rib (140) are configured to slide within adjacent distally presented pockets (143, 145), respectively, during articulation of articulating distal portion (130).

Arched proximally presented protrusions (144, 164) may be at least partially housed within corresponding pockets (145, 155) in both a straight configuration and an articulated configuration. However, top linear proximally presented protrusions (142, 162) may not be housed within corresponding pockets (143, 153) while initially in the straight configuration, but may be housed within corresponding pockets (143, 153) while in the articulated configuration. However, this arrangement is merely optional, as all protrusions (142, 144, 162, 164) may be partially housed within corresponding pockets (143, 145, 153, 155) in the straight configuration; no protrusions (142, 144, 162, 164) may be partially housed within corresponding pockets (143, 145, 153, 155) in the straight configuration; or any other suitable combination/pattern of housing protrusions (142, 144, 162, 164) within corresponding pockets (143, 145, 153, 155) based on the articulated state of distal portion (130) may be used as would be apparent to one having ordinary skill in the art in view of the teachings herein.

The interaction between proximally presented protrusions (142, 144, 162, 164) and corresponding pockets (143, 145, 153, 155) may help promote sufficient rigidity during insertion of guide catheter (100). For instance, the arched profile of protrusions (144, 164) and pockets (145, 155) may prevent external forces from accidentally articulating distal portion (130) in response to external forces exerted on guide catheter (130). Unless the force profile exerted on the guide catheter (100) corresponds to the arched profile of protrusions (144, 164) and pockets (145, 155), the frictional breaking force provided between the interaction of protrusions (144, 164) and pockets (145, 155) may resist unwanted articulation of guide catheter (100). In other words, the arched profile of protrusions (144, 164) and pockets (145, 155) may require a specific and consistent change in direction of an external force to manipulate articulating distal portion (130) to articulate/bend. It should be understood that translation of pull wire (120) may be configured to provide this consistent and constant change in force direction to articulate/bend guide catheter (100).

As mentioned above, each articulating rib (140) includes a proximal angled surface (146) and a distal angled surface (148), while distal rib (160) includes a proximal surface (166) and rigid portion (150) includes a distal surface (158). During articulation of articulating distal portion (130), proximal angled surfaces (146, 166) are configured to abut against corresponding and adjacent distal angled surfaces (148, 158) such that when articulation distal portion (130) is completely articulated, proximal angled surfaces 9146, 166) are flush against corresponding and adjacent distal angled surfaces (148, 158). The interaction between angled surfaces (146, 148,158, 166) may help promote articulation in repose to translation of pull wire (120). Additionally, interaction of angled surfaces (146, 148, 158, 166) may help create a smooth interior lumen defined by articulating distal portion (130) to help accommodate longitudinal translation of dilator (22) within lumen.

While in the current example, pull wires (120) extend along the exterior of guide catheter (100), it should be understood that this is merely optional. Pull wires (120) may extend along guide catheter in the interior of guide catheter (100), within a predefined, separate lumen dimensioned to slidably house pull wires (120), or any other suitable arrangement that would be apparent to one having ordinary skill in the art in view of the teachings herein.

Figure 12:
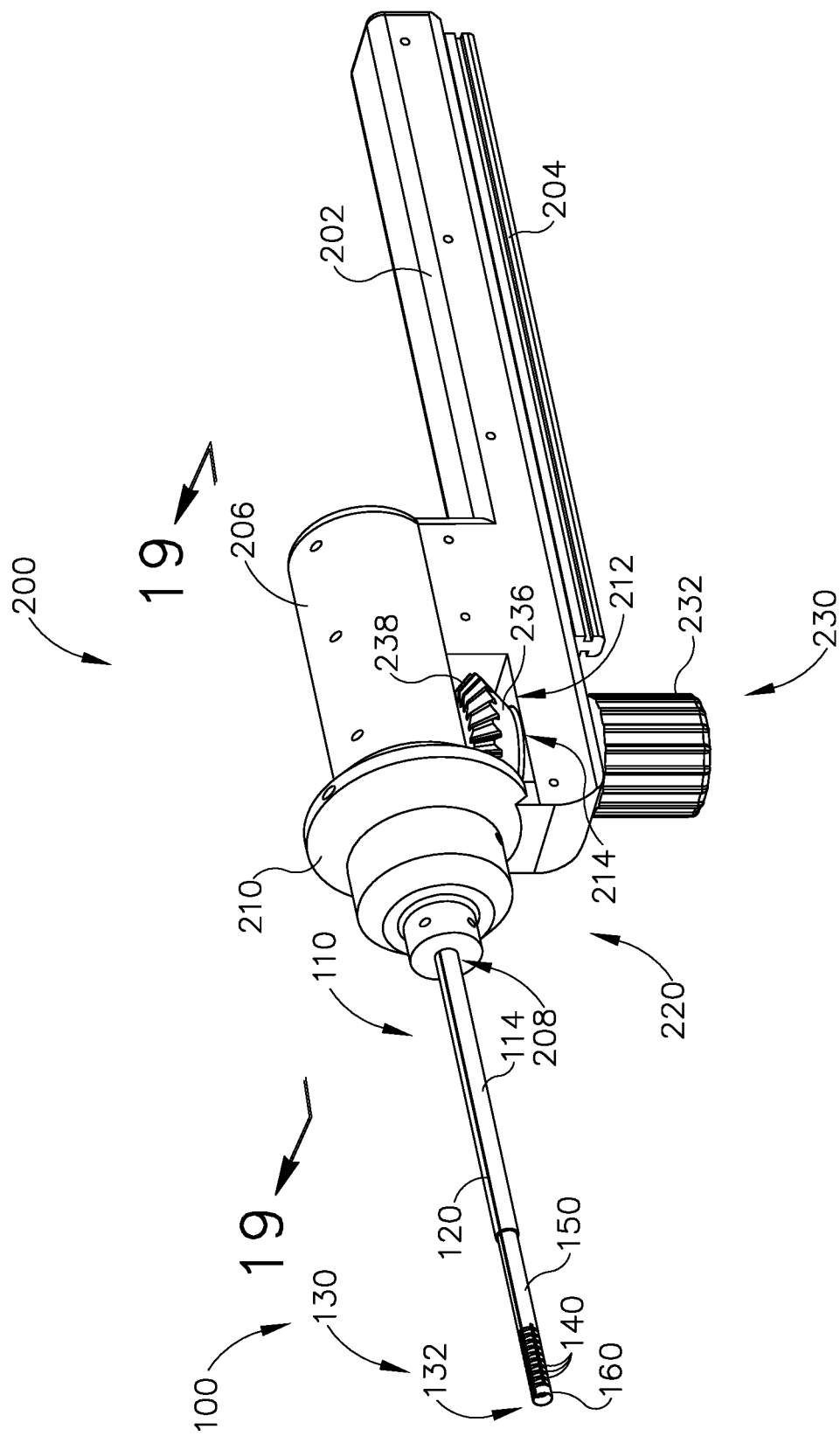
FIG. 12 depicts a perspective view of the guide catheter of FIG. 8 attached to an exemplary guide catheter handle, both of which may be readily incorporated into the exemplary dilation catheter system of FIG. 1.
Figure 13:
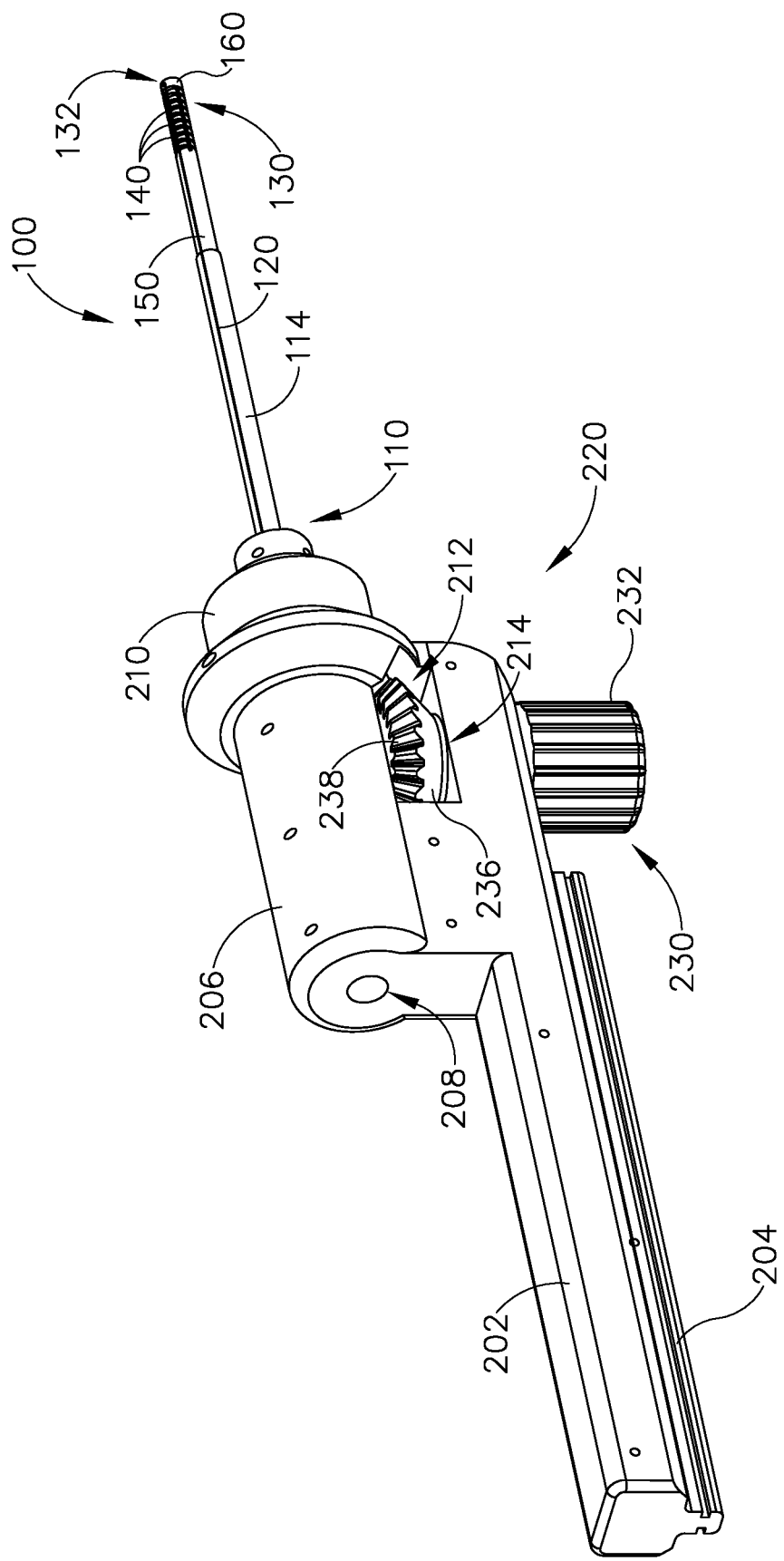
FIG. 13 depicts another perspective view of the guide catheter of FIG. 8 attached to the guide catheter handle of FIG. 12.
Figure 14:
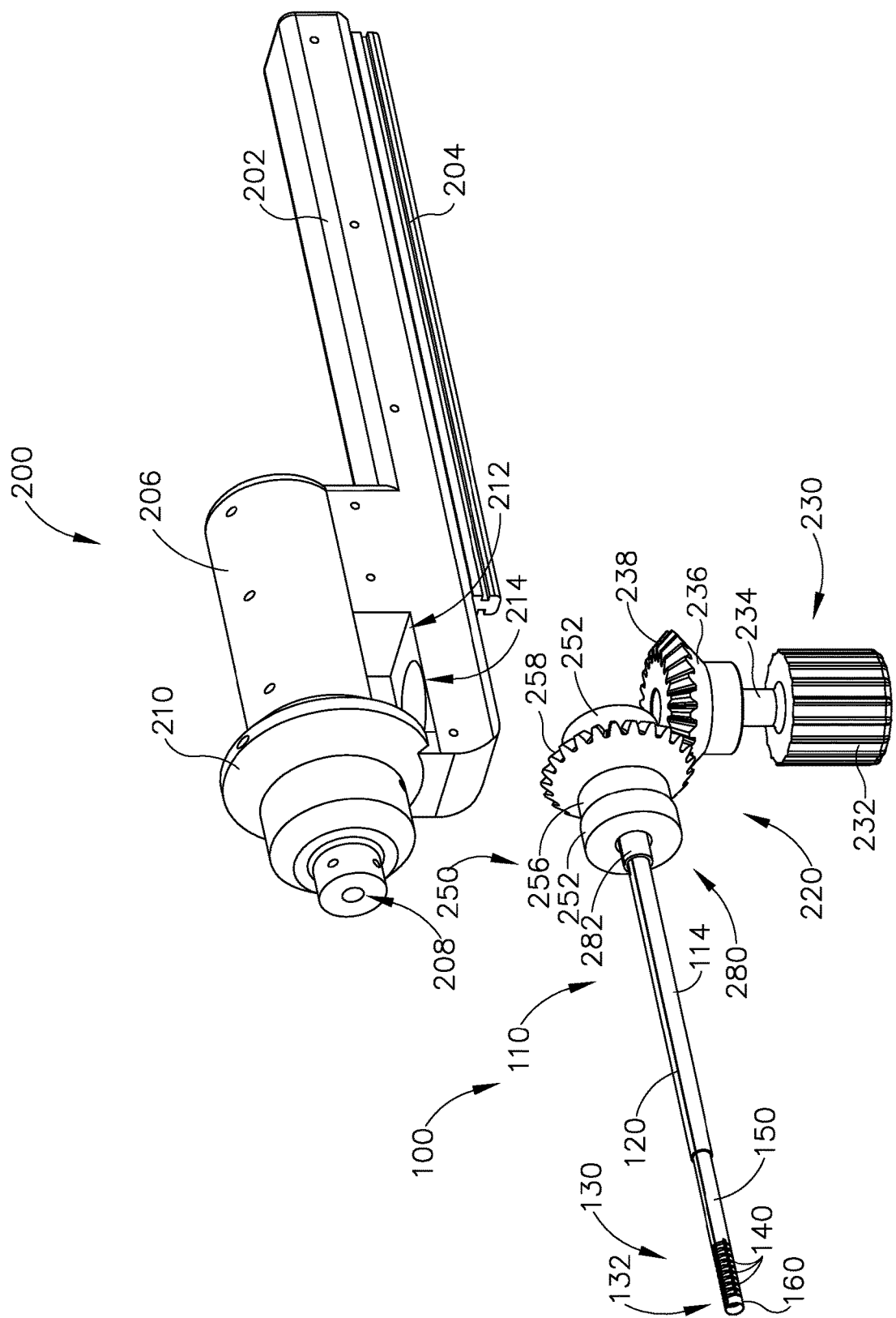
FIG. 14 depicts an exploded perspective view of the guide catheter of FIG. 8 and the guide catheter handle of FIG. 12.
Figure 15:
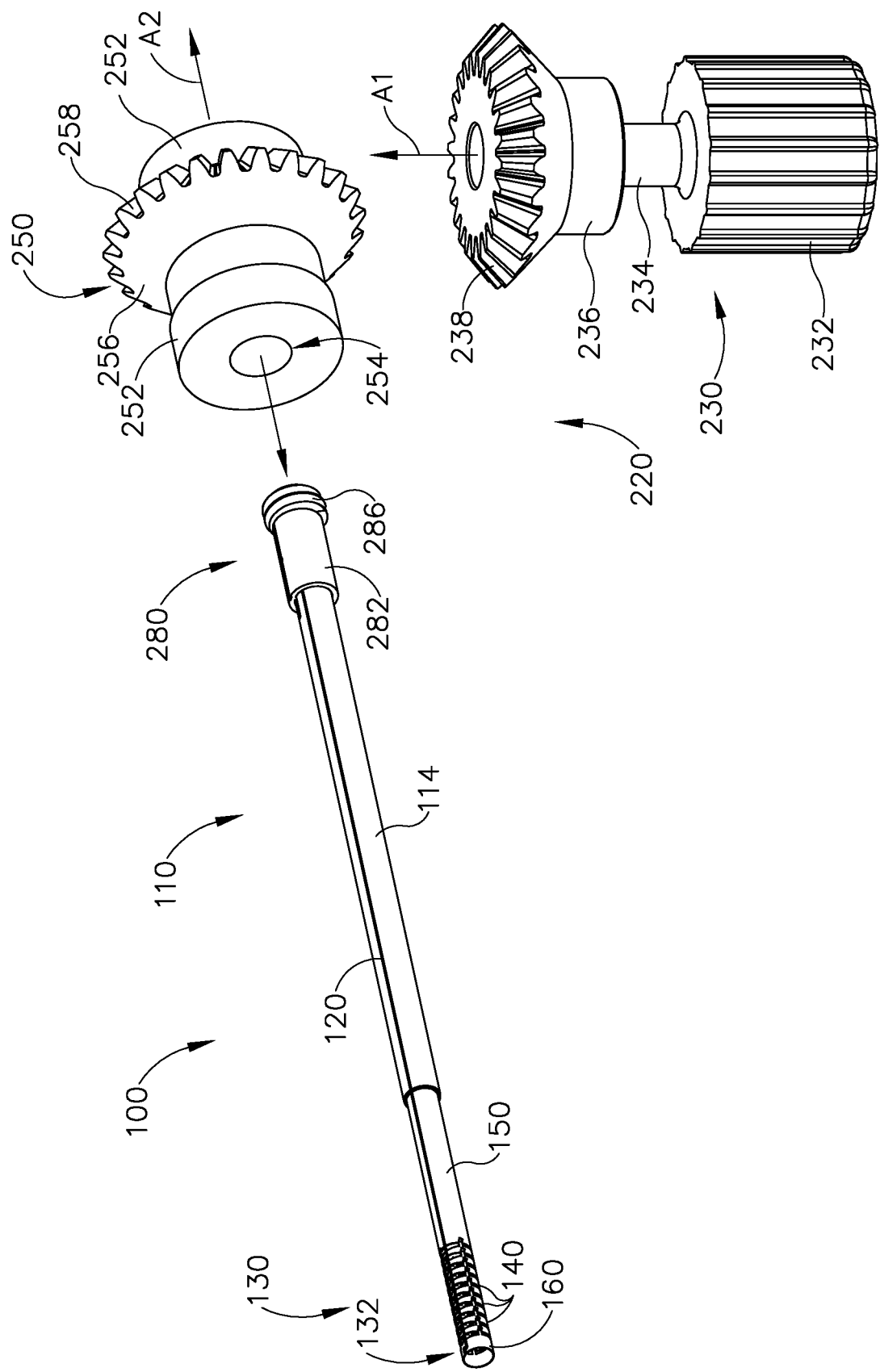
FIG. 15 depicts an exploded perspective view of the guide catheter of FIG. 8 and a guide catheter articulation assembly of the guide catheter handle of FIG. 12.

FIGS. 12-14 show guide catheter (100) coupled to an exemplary guide catheter handle (200) such that the two may be readily incorporated into dilation catheter system (10) described above, in place of guide catheter (30). Guide catheter handle (200) includes a proximal elongated body (202), a T-rail (204) extending along the bottom of proximal elongated body (202), a catheter housing (206) above and distal in relation to proximal elongated body (202), an articulation housing (210), and a guide catheter articulation assembly (220). As will be described in greater detail below, guide catheter articulation assembly (220) is operatively coupled with a proximal end of pull wire (120) such that guide catheter articulation assembly (220) may translate pull wire (120) relative to rigid shaft (114). As mentioned above, and as will be further described below, translation of pull wire (120) may drive articulation of articulating distal portion (130). Additionally, as will be described in greater detail below, guide catheter articulation assembly (220) may be configured to selectively maintain the longitudinal location of pull wire (120) relative to rigid shaft (114) in order to maintain the articulated configuration of articulation distal portion (130).

T-rail (204) may be dimensioned to selectively couple with a handle extension, such as a handle extension comprising finger pegs to promote grasping of the instrument with a single hand. Proximal elongated body (202) may slidably couple with a first slidable body operatively coupled with dilation catheter (20) and a second slidable body operatively coupled with guide wire (50). Therefore, an operator may translate and/or rotate first body and second body relative to elongated body (202) in order to translate and/or rotate dilation catheter (20) or guide wire (50) relative to both guide catheter handle (200) and guide catheter (100). When properly coupled together in accordance with the description above, an operator may manipulate dilation catheter (20), guide wire (50), and guide catheter (100) with a single hand.

Rigid shaft (114) extends distally from and is fixed to articulation housing (210). Articulation housing (210) and catheter housing (206) define a pathway (208) configured to slidably receive dilation catheter (20), such that dilation catheter (20) may be inserted through pathway (208) in order to be inserted through the lumen defined by guide catheter (100).

Articulation housing (210) also defines an opening (212) and a through bore (214) to selectively house portions of guide catheter articulation assembly (220). Guide catheter articulation assembly (220) includes a first rotary assembly (230), a second rotary assembly (250), and a translating assembly (280). As will be described in greater detail below, first rotary assembly (230) is configured to rotate second rotary assembly (250); while second rotary assembly (250) is configured to translate translating assembly (280) in order to longitudinally translate pull wire (120) relative to rigid shaft (114), and thereby articulate/bend articulating distal portion (130).

First rotary assembly (230) includes a rotatable grip (232), a shaft (234), and a first bevel gear (236) having a plurality of teeth (238). Shaft (234) is rotatably disposed within through bore (214), whiles first bevel gear (236) is rotatably housed within opening (212). Rotatable grip (232), shaft (234), and first bevel gear (236) are unitarily connected, such that rotation of rotatable grip (232) leads to rotation of shaft (234) and first bevel gear (236). Rotatable grip (232) extends below the portion of articulation housing (210) defining through bore (214). Rotatable grip (232) is positioned to be accessible to an operator grasping guide catheter handle (200) with one hand. Therefore, an operator may rotate rotatable grip (232) relative to articulation housing (210) about a first axis (A1) in order to rotate both shaft (234) and first bevel gear (236) relative to articulation housing (210) about first axis (A1) as well.

Second rotary assembly (250) includes a second bevel gear (256) disposed between two washers (252), all of which are housed within a chamber (216) defined by articulation housing (210). Second bevel gear (256) is rotably housed within chamber (216) such that second bevel gear (256) may rotate relative to articulation housing assembly (210) about a second axis (A2). Second bevel gear (256) include a plurality of teeth (258) configured to complementary mesh with teeth (238) of first bevel gear (236). Therefore, rotation of first bevel gear (236) in a first angular direction about first axis (A1) will lead to rotation of second bevel gear (256) in a second angular direction about second axis (A2) via interaction between teeth (238, 258). Conversely, rotation of first bevel gear (236) in a third angular direction, opposite the first angular direction, about first axis (A1) will lead to rotation of second bevel gear (256) in a fourth angular direction, opposite second angular direction, about second axis (A2) via interaction between teeth (238, 258).

Figure 18:
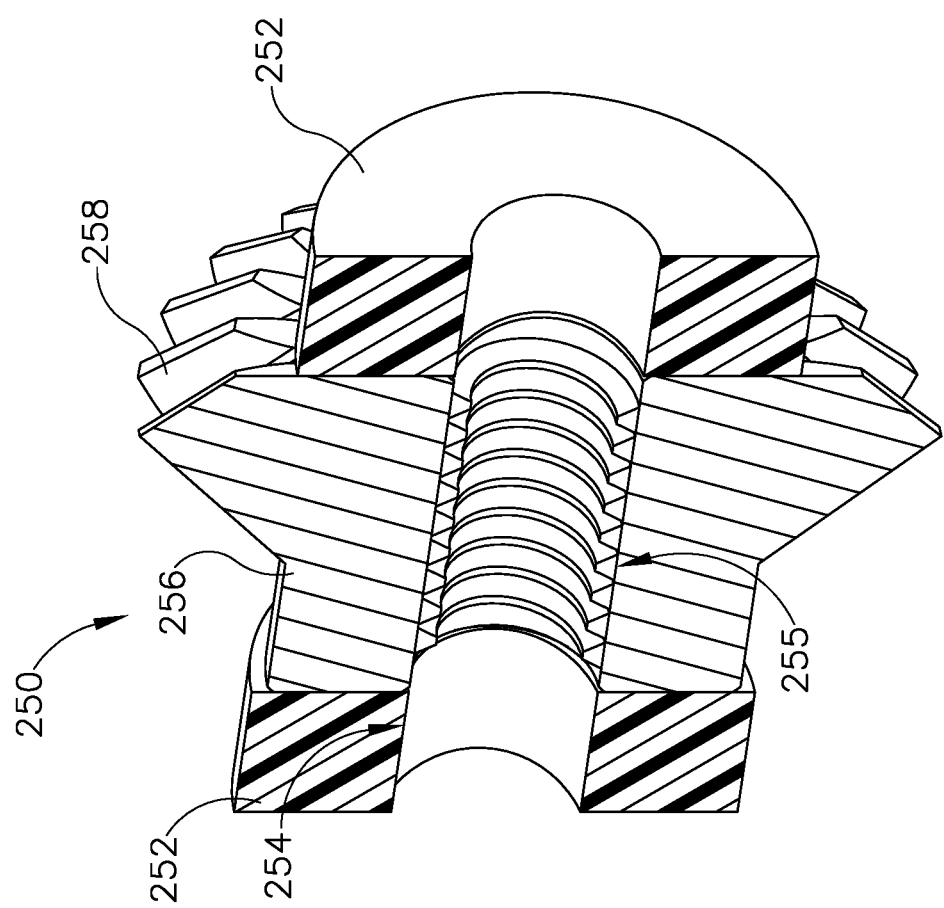
FIG. 18 depicts a cross-sectional perspective view of the rotary assembly of FIG. 17, taken along line 18-18 of FIG. 17.

Additionally, second rotating assembly (250) defines a pathway (254) which connects pathway (208) defined by catheter housing (206) and articulation housing (210) with the lumen of guide catheter (100). Therefore, dilation catheter (20) may be slidably housed within the lumen of guide catheter (100), pathway (254) of second rotary assembly (250), and pathway (208) of catheter housing (206) and articulation housing (210). As best seen in FIG. 18, the portion of pathway (254) defined by second bevel gear (256) includes threading (255). As will be described in greater detail below, threading (255) is configured to mesh with threading (286) of translating assembly (280) such that rotation of second bevel gear (256) about second axis (A2) leads to translation of translating assembly (280) and pull wire (120), thereby bending articulating distal portion (130) of guide catheter (100).

Figure 16:
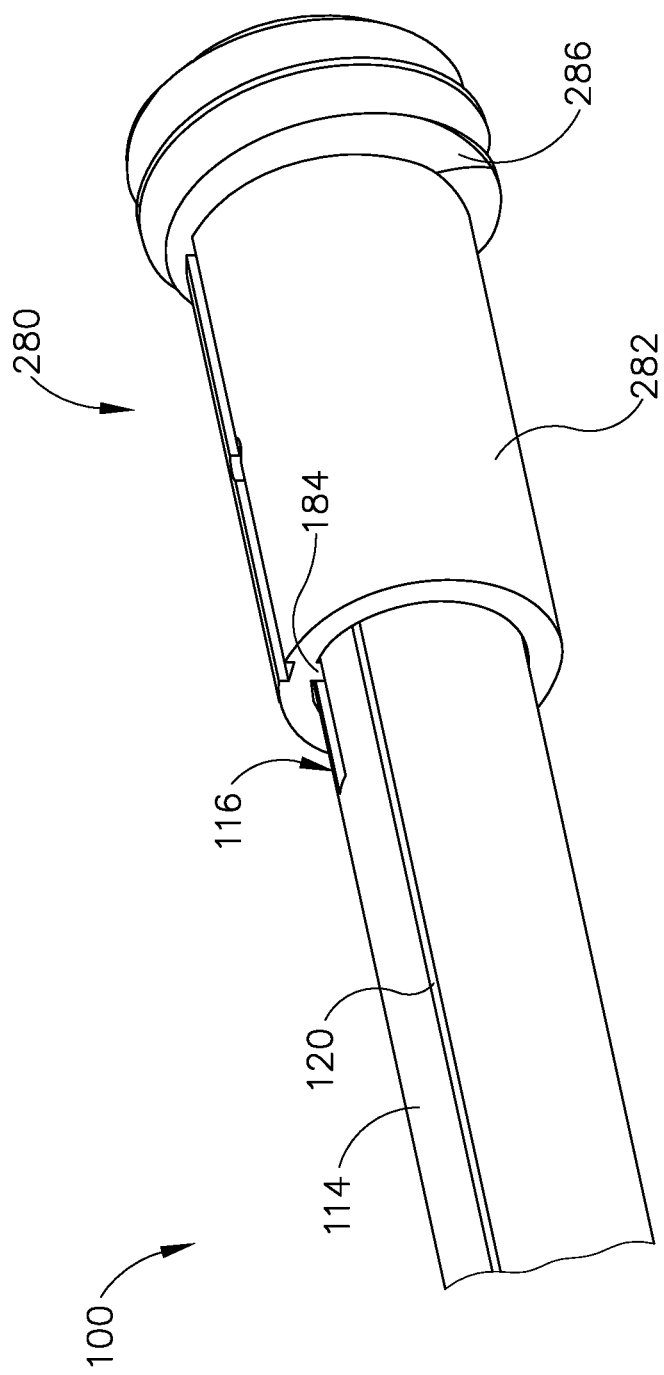
FIG. 16 depicts a perspective view of the guide catheter of FIG. 8 and a translating assembly of the guide catheter articulation assembly of FIG. 15.
Figure 17:
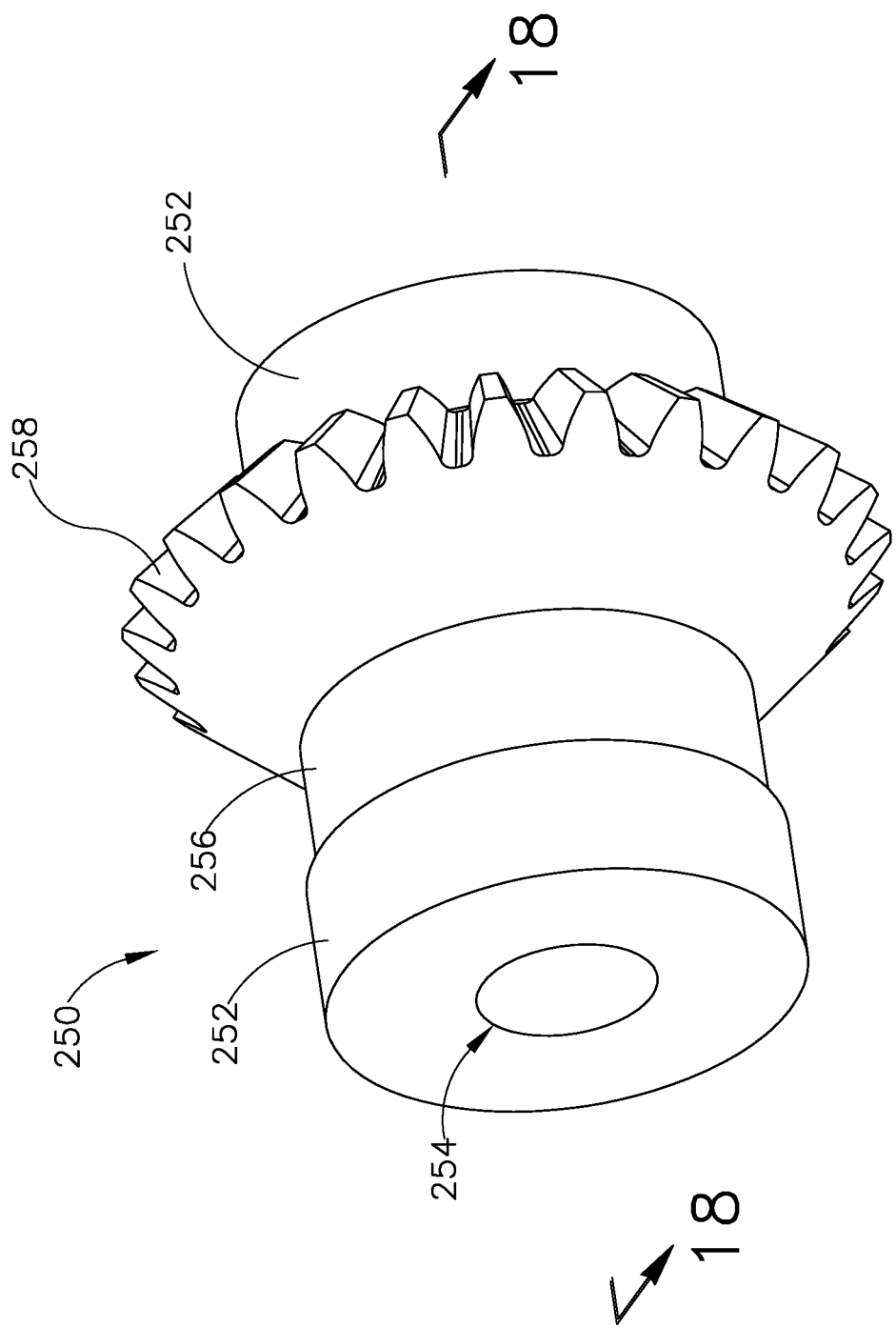
FIG. 17 depicts a perspective view of a rotary assembly of the guide catheter articulation assembly of FIG. 15.

As best seen in FIG. 16, translating assembly (280) includes a translating sleeve (282) unitarily coupled with threading (286). Translating sleeve (282) is coupled with the proximal end of pull wire (120) such that translation of translating sleeve (282) leads to translation of pull wire (120) relative to rigid shaft (114). Threading (286) meshes with threading (255) of second rotating assembly (250) such that at least a portion of translating assembly (280) is housed within pathway (254) of second rotary assembly (250). Additionally, translating sleeve (282) includes a keyed member (184) slidably housed within a slot (116) located at the proximal end of rigid shaft (114). Keyed member (284) is housed within slot (116) of rigid shaft (114) such that translating sleeve (282) and threading (286) may not rotate relative to rigid shaft (114) about second axis (A2), but may only translate relative to rigid shaft (114).

As described above, rigid shaft (114) is fixed to articulation housing (210). Therefore, as second bevel gear (256) rotates relative to articulation housing (210) about second axis (A2), threading (255) of second rotary assembly (250) also rotates relative to articulation housing (210) about second axis (A2). Because threading (286) of translating assembly (280) meshes with threading (255) of second rotating assembly (250), and because translating assembly (280) is rotatable fixed about second axis (A2), rotation of second bevel gear (256) drives translation of translating assembly (280) relative to rigid shaft (114) via interaction between threading (255, 286).

Figure 19A:
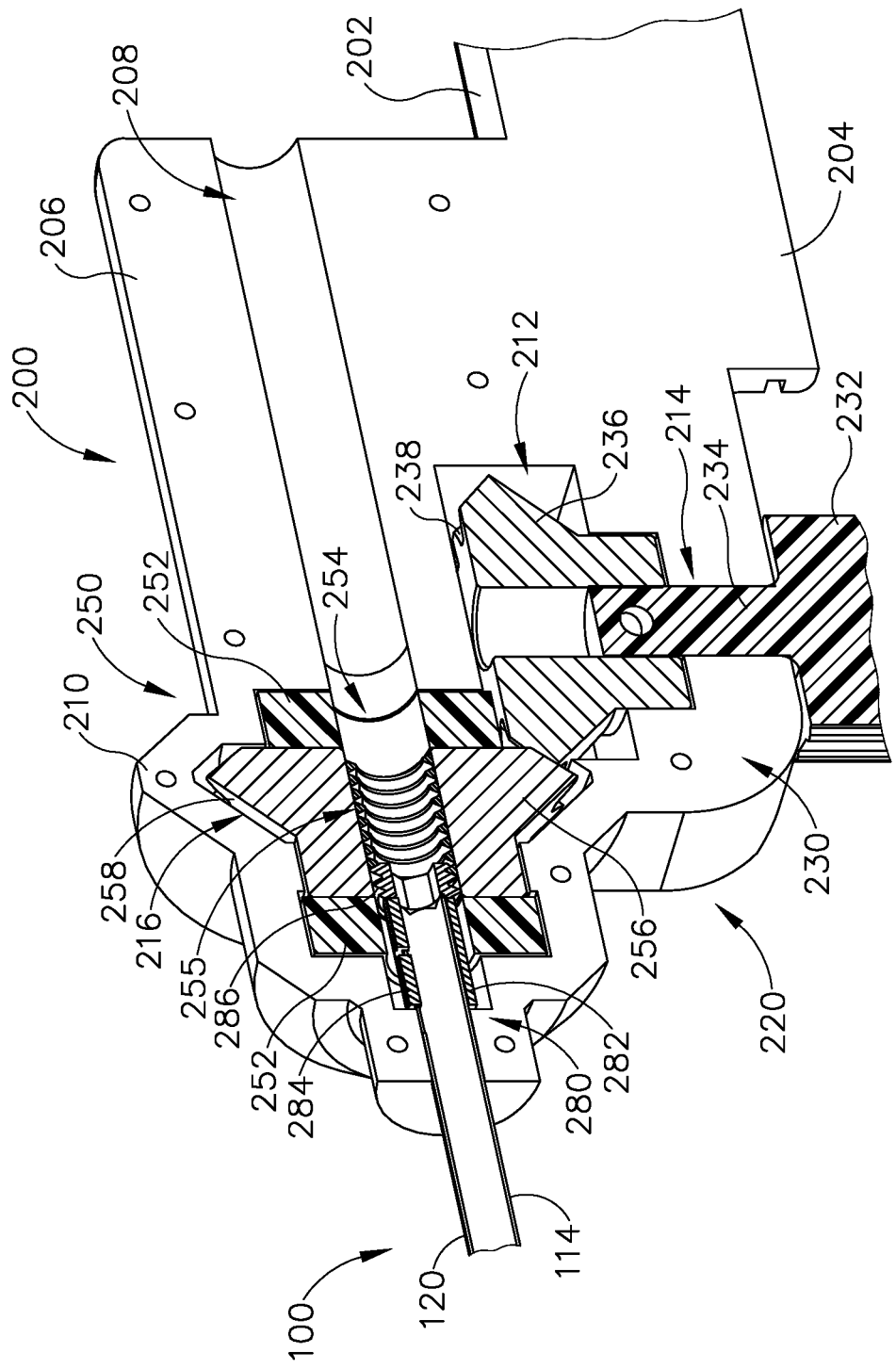
FIG. 19A depicts a cross-sectional perspective view of the guide catheter of FIG. 8 attached to the exemplary guide catheter handle of FIG. 12, where the guide catheter articulation assembly of FIG. 15 is in a first position, taken along line 19-19 of FIG. 12.
Figure 19B:
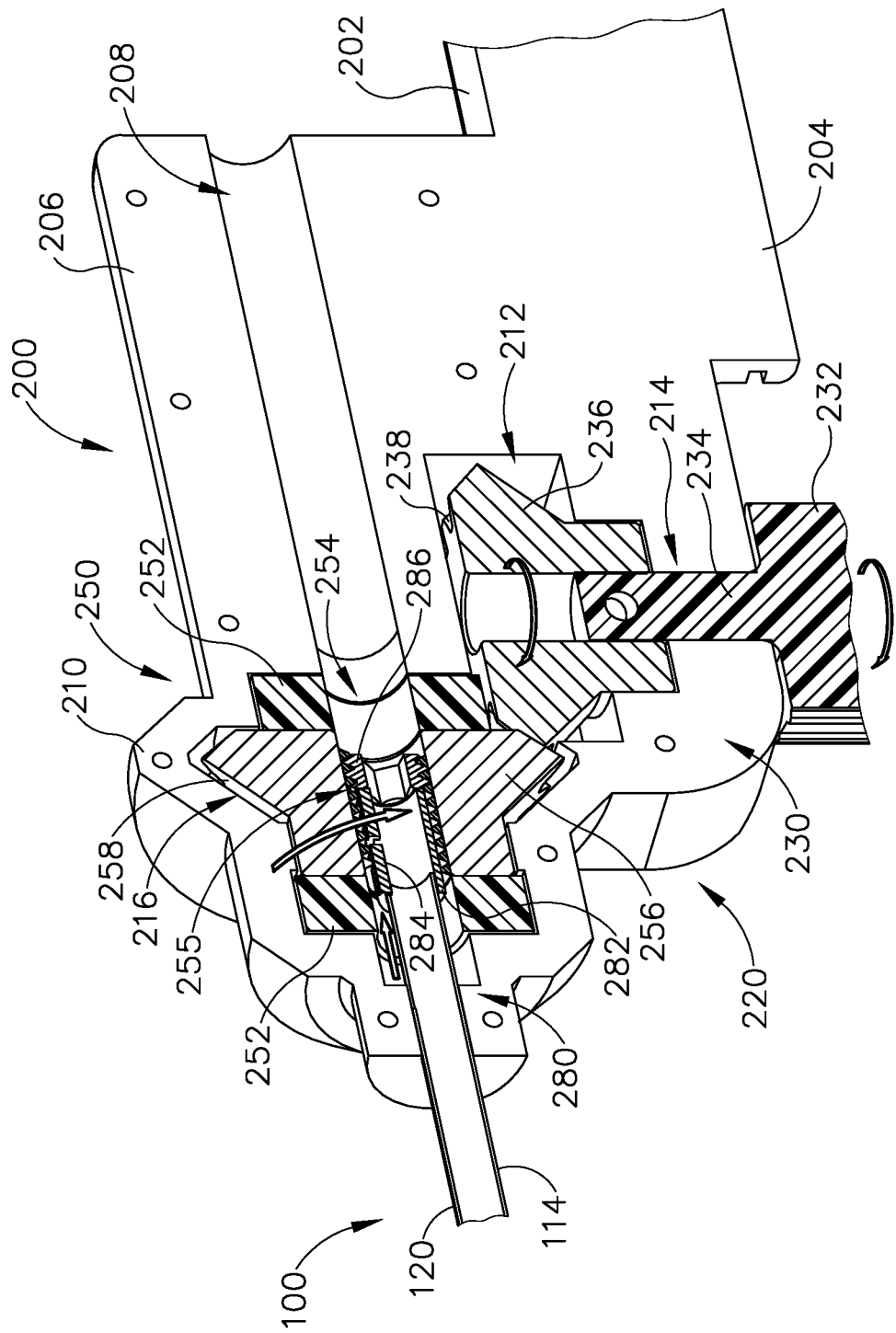
FIG. 19B depicts a cross-sectional perspective view of the guide catheter of FIG. 8 attached to the exemplary guide catheter handle of FIG. 12, where the guide catheter articulation assembly of FIG. 15 is in a second position, taken along line 19-19 of FIG. 12.

FIGS. 19A-20B show an exemplary use of guide catheter handle (200) used while operatively coupled with guide catheter (100) to articulate articulating distal portion (130). FIG. 19A shows translating assembly (280) and pull wire (120) in a distal position, while FIG. 20A shows distal articulation portion (130) in the straight configuration corresponding to pull wire (120) in the distal position. If an operator desires to articulate distal articulation portion (130) of guide catheter (100) in order to suitably access a desired nasal cavity, an operator may rotate rotatable grip (232) in the first angular direction about first axis (A1). This rotation of rotatable grip (232) will also rotate shaft (234) and first bevel gear (236) in the first angular direction about first axis (A1). Because first bevel gear (236) and second bevel gear (256) have teeth (238, 258) that mesh, rotation of first bevel gear (236) about first axis (A1) in the first direction causes rotation of second bevel gear (256) in the second direction about second axis (A2). Rotation of second bevel gear (256) in the second angular direction about second axis (A2) also causes rotation of threading (255) in the second angular direction about second axis (A2). Rotation of threading (255) drives translating assembly (280) in the proximal direction due to interaction between threading (255, 286) and the fact translating assembly (280) is rotationally fixed about second axis (A2).

Proximal translation of translating assembly (280) leads to proximal translation of pull wire (120). As best seen between FIGS. 20A-20B, proximal translation of pull wire (120) leads to articulation of articulating distal portion (130). In particular, pull wire (120) pulls distal rib (160) toward the distal most articulating rib (140). The resilient nature of resilient spine (170) allows resilient spine (170) to bend from a natural position (shown in FIG. 20A) to a flexed position (shown in FIG. 20B). Flexing of resilient spine (170) allows proximally angled surfaces (146, 166) to rotate toward adjacent distally angled surfaces (148, 158). Additionally, side arched proximally presented protrusions (144, 164) of articulating ribs (140) and distal rib (160) slide into corresponding side arched distally presented pockets (145, 155) of articulating ribs (140) and rigid portion (150). Additionally, top linear proximally presented protrusions (146, 166) of articulating ribs (140) and distal rib (160) slide into corresponding top linear distally presented pockets (143, 153). The interaction between protrusions (144, 146, 164, 166) and corresponding pockets (143, 145, 153, 155) may help form the predetermined articulated bend as shown in FIG. 20B; as well as add to rigidity of the articulation bend as described above. Additionally, the interaction between proximal angled surfaces (146, 166) and corresponding adjacent distal angled surfaces (148, 158) may promote forming the predetermined articulated bend, as well as create a flush lumen defined by the bent portion of guide catheter (100).

Interaction between threading (286) of translating assembly (280) and threading (255) of second rotary assembly (250) may provide a frictional breaking force, which may help prevent unwanted actuation of translating assembly (280) and pull wire (120), thereby helping prevent unwanted articulation of articulating distal portion (130) in response to external forces.

Figure 20A:
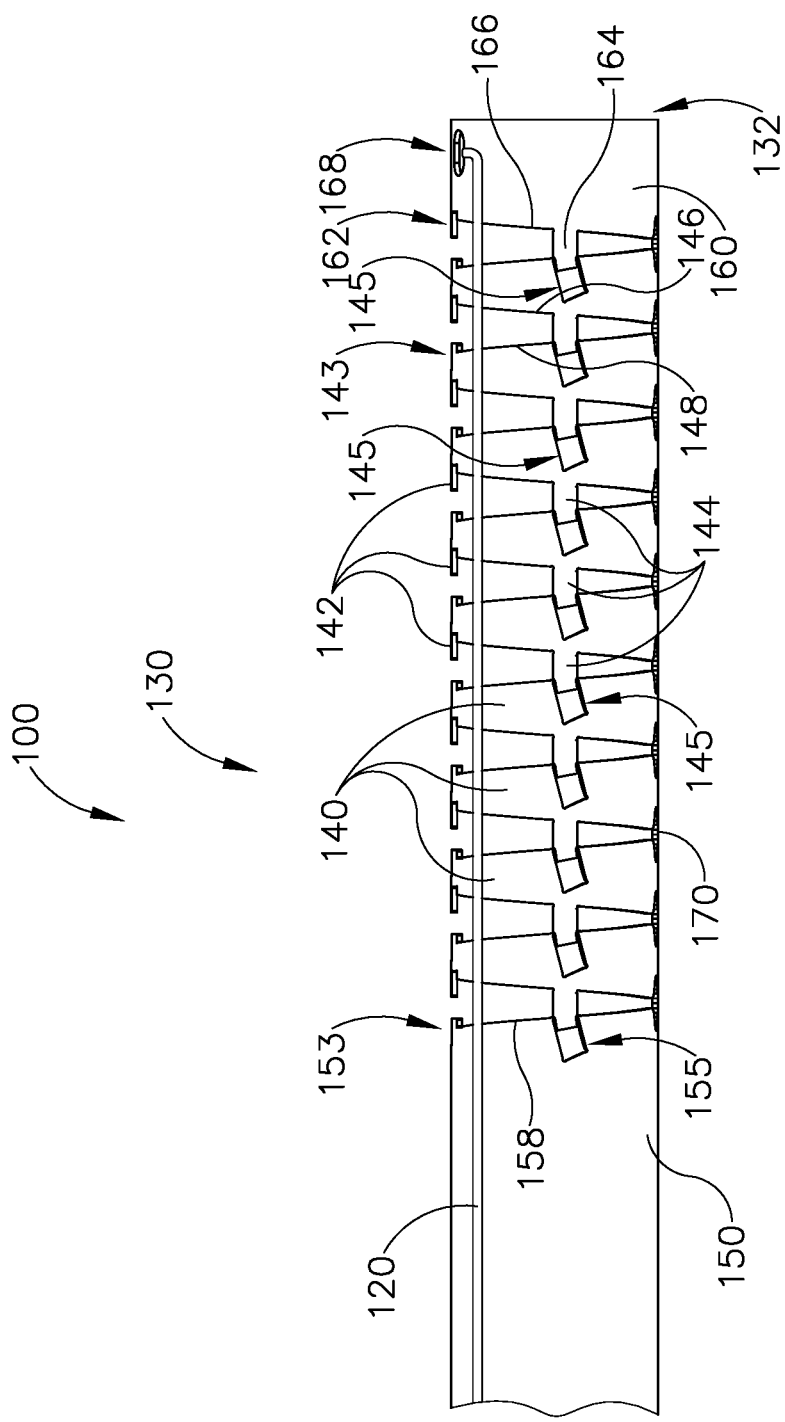
FIG. 20A depicts a side elevational view of the distal end of the guide catheter of FIG. 8, where the guide catheter is in a straight, unarticulated, configuration.
Figure 20B:
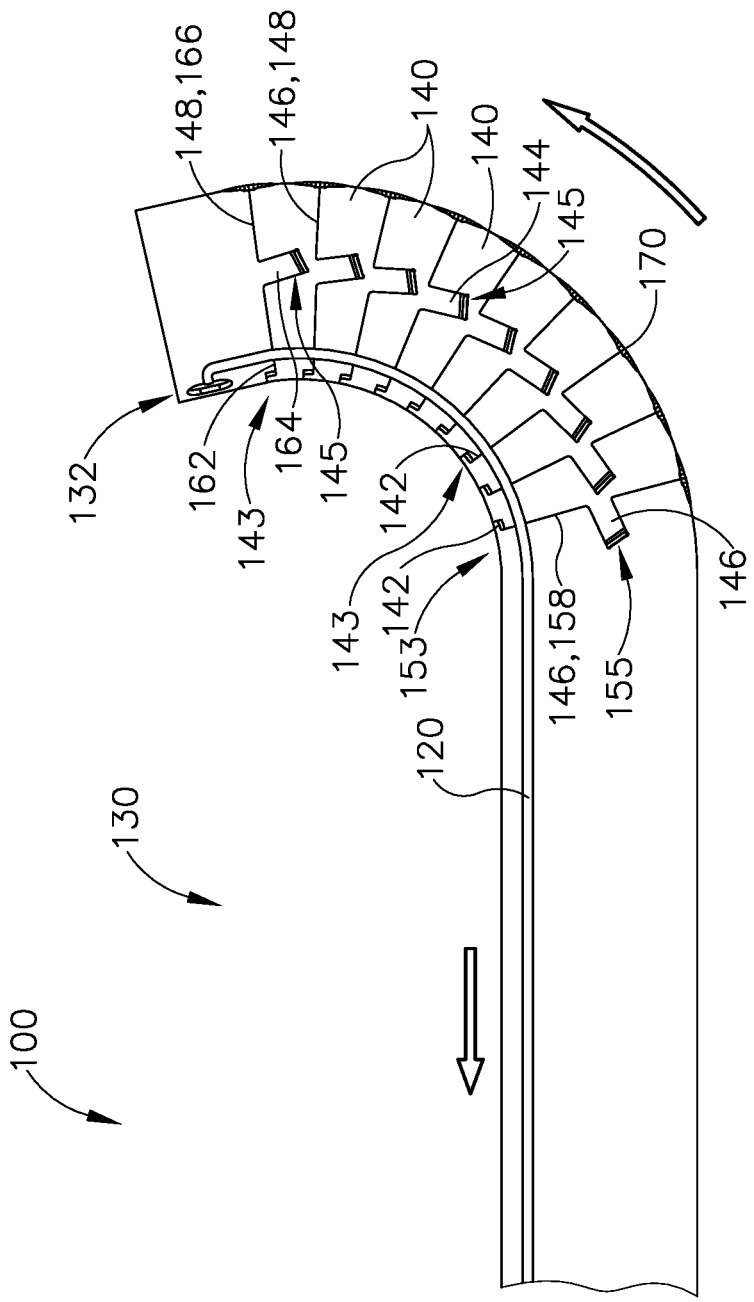
FIG. 20B depicts a side elevational view of the distal end of the guide catheter of FIG. 8, where the guide catheter is in a curved, articulated, configuration.
Figure 21:
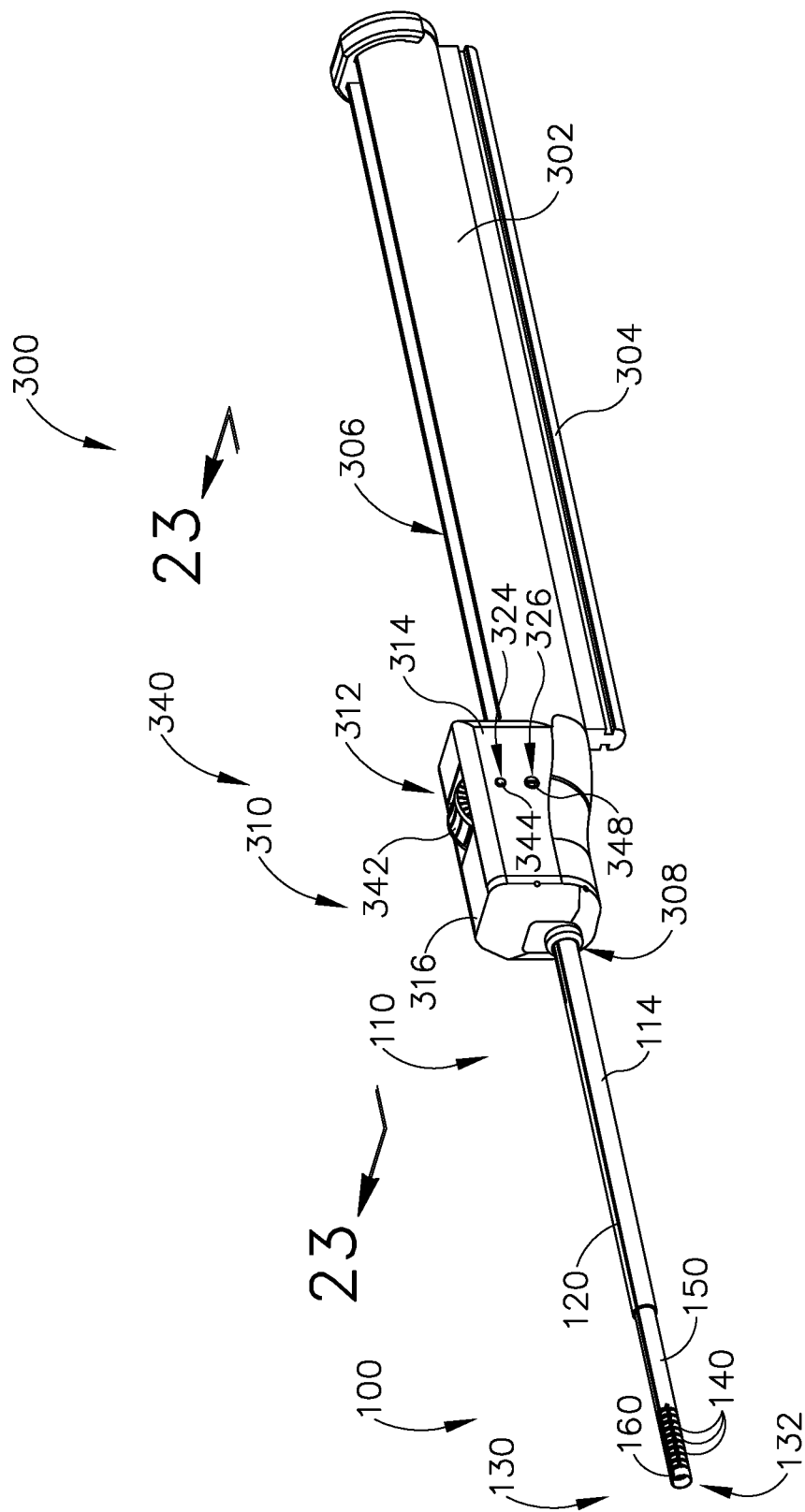
FIG. 21 depicts a perspective view of the guide catheter of FIG. 8 attached to another exemplary guide catheter handle, both of which may be readily incorporated into the exemplary dilation catheter system of FIG. 1.

If an operator desires to articulate/bend articulating distal portion (130) from the bent configuration shown in FIG. 20B to the straight configuration shown in FIG. 20A, an operator may rotate rotatable grip (232) in the third rotational direction, opposite the first rotational direction, about first axis (A1), which may then rotate second bevel gear (286) in the fourth rotational direction, opposite the second rotational direction, about the second axis (A2), in accordance with the teachings above. This may in turn distally drive translating assembly (280) and pull wire (120) distally to the position shown in FIG. 19A, thereby allowing resilient spine (170) to flex back to its natural position and thereby bend articulating distal portion (130) back to the position shown in FIG. 20A. It should be understood that it is the longitudinal position of the proximal end of pull wire (120) attached to translating assembly (280) that provides the force to help flex resilient spine (170) to the flexed position shown in FIG. 20B. Therefore, when pull wire (120) and translating assembly (180) are returned to the distal position shown in FIG. 19A, the resilient nature of resilient spine (170) may flex articulating distal portion (130) back to the position shown in FIG. 20A.

FIGS. 21-23B show guide catheter (100) coupled to another exemplary handle (300) such that the two may be readily incorporated into dilation catheter system (10) described above, in place of guide catheter (30). Guide catheter handle (300) includes a proximal elongated body (302) defining a slide channel (306), a T-rail (304) extending along the bottom of proximal elongated body (302), an articulation housing assembly (310), and a guide catheter articulation assembly (340). As will be described in greater detail below, guide catheter articulation assembly (340) is operatively coupled with a proximal end of pull wire (120) such that guide catheter articulation assembly (340) may translate pull wire (120) relative to rigid shaft (114). As described above, translation of pull wire (120) may drive articulation of articulating distal portion (130). Additionally, as will be described in greater detail below, guide catheter articulation assembly (340) may be configured to selectively maintain the longitudinal location of pull wire (120) relative to rigid shaft (114) in order to maintain the articulated configuration of articulation distal portion (130).

T-rail (304) may be dimensioned to selectively couple with a handle extension, such as a handle extension comprising finger pegs to promote grasping of the instrument with a single hand. Slide channel (306) of proximal elongated body (302) may slidably couple with a first slidable body operatively coupled with dilation catheter (20) and a second slidable body operatively coupled with guide wire (50). Therefore, an operator may translate and/or rotate first body and second body relative to elongated body (302) in order to translate and/or rotate dilation catheter (20) or guide wire (50) relative to both guide catheter handle (300) and guide catheter (100). When properly coupled together in accordance with the description above, an operator may manipulate dilation catheter (20), guide wire (50), and guide catheter (100) with a single hand.

Rigid shaft (114) extends distally from and is fixed to articulation housing (310). Articulation housing (310) defines a pathway (308) configured to slidably receive dilation catheter (20), such that dilation catheter (20) may be inserted through pathway (308) in order to be inserted through the lumen defined by guide catheter (100).

Articulation housing assembly (310) includes a first portion (314) and a second portion (316) that cooperative define an opening (312) and a chamber (318). Chamber (318) is dimensioned to house guide catheter articulation assembly (340) while opening (312) provides access to a rotary wheel (342) of guide catheter articulation assembly (340). As will be described in greater detail below, rotation of rotary wheel (342) is configured to longitudinally translate pull wire (120) in order to articulate/bend articulating distal portion (130) in accordance with the description above. First portion (314) also defines a pin hole (324) and a threaded hole (326), which are dimensioned to couple with a pin (344) and a ball nose spring plunger (348), respectively. Second portion (316) includes a pair of proximally presented arms (320) that define a translating pathway (322)

Figure 22:
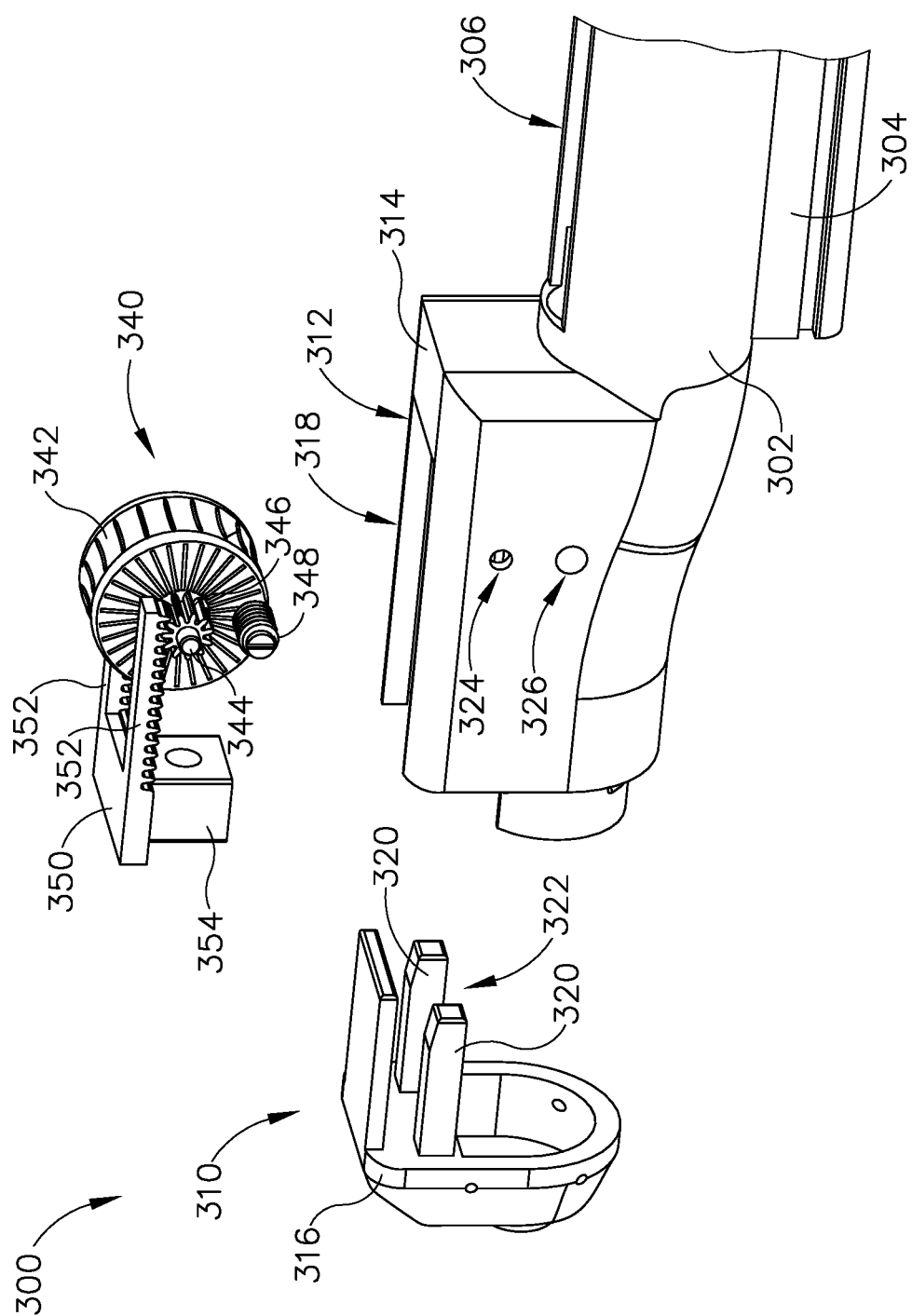
FIG. 22 depicts an exploded perspective view of the guide catheter handle of FIG. 21.

As best seen in FIG. 22, guide catheter articulation assembly (340) includes rotary wheel (342), pin (344) extending through the center of rotary wheel (344), a pair of pinions (344) disposed around pin (344) on opposite sides of rotary wheel (342), a pair of ball nose spring plungers (348) located on opposite sides of rotary wheel (342), and a translating member (350). Translating member (350) includes a pull wire coupler (354) unitarily attached to a pair of racks (352) extending proximally from pull wire coupler (354). Pull wire coupler (354) is configured to fix to a proximal end of pull wires (120) such that translation of translating member (350) relative to articulation housing assembly (310) leads to translation of pull wires (120) relative to rigid shaft (114). Racks (352) slidably rest on top of proximally presented arms (320) while pull wire coupler (354) is slidably housed within translating pathway (322) defined by proximally presented arms (320). Racks (352) mesh with corresponding pinions (346).

Pin (344) extends through pin hole (324) of first portion (314) of articulation housing assembly (310). Rotary wheel (344) and pinions (344) may unitarily rotate together relative to articulation housing assembly (310) about pin (344). Therefore, rotary wheel (344) and pinions (344) are rotatably coupled to first portion (314) of articulation housing assembly (310).

Figure 23A:
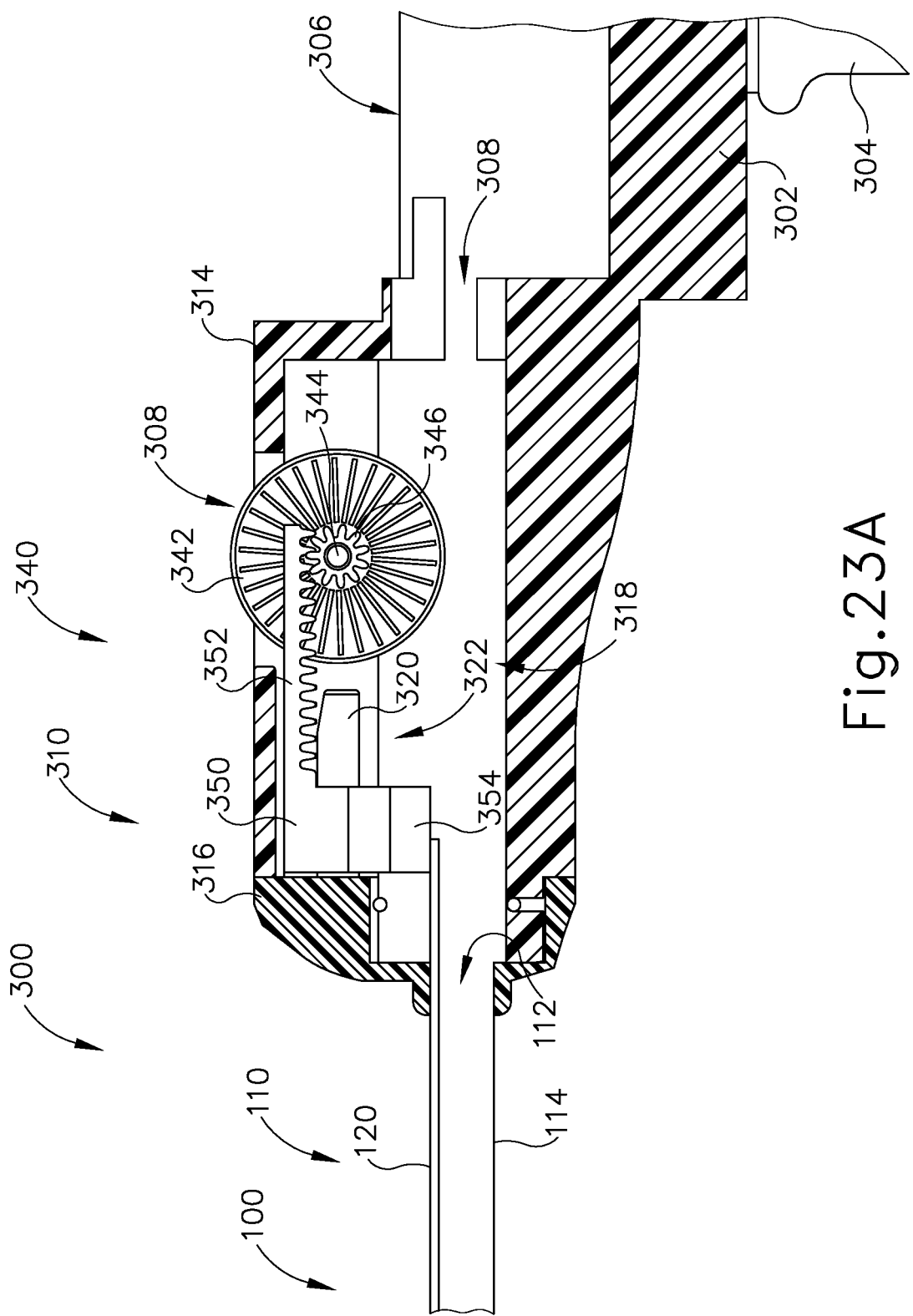
FIG. 23A depicts a cross-sectional side view of the guide catheter of FIG. 8 attached to the guide catheter handle assembly of FIG. 21, where a guide catheter articulation assembly of the guide catheter handle assembly is in a first position, taken along line 23-23 of FIG. 21.
Figure 23B:
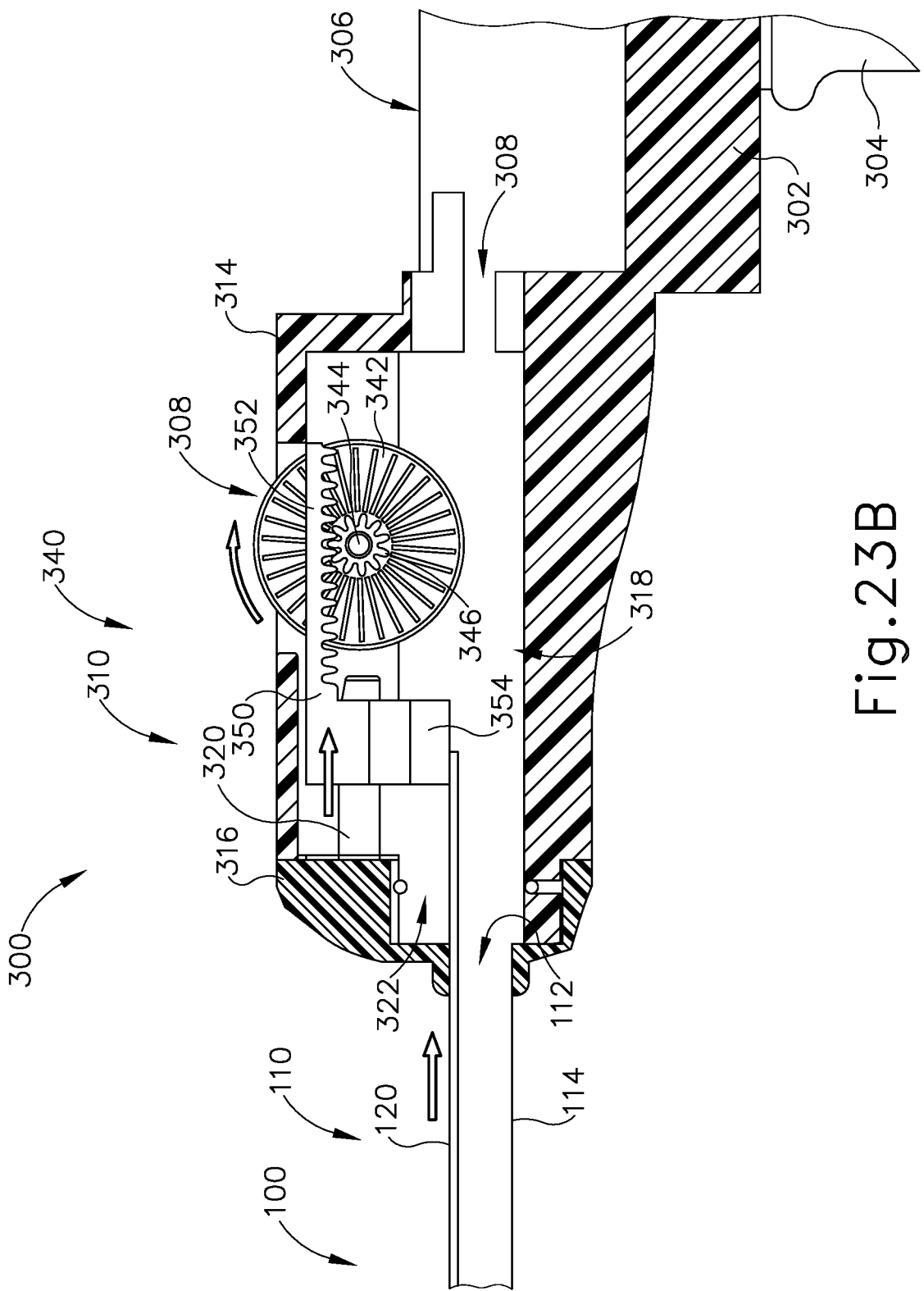
FIG. 23B depicts a cross-sectional side view of the guide catheter of FIG. 8 attached to the guide catheter handle assembly of FIG. 21, where the guide catheter articulation assembly of FIG. 23A is in a second position, taken along line 23-23 of FIG. 21.
Figure 24:
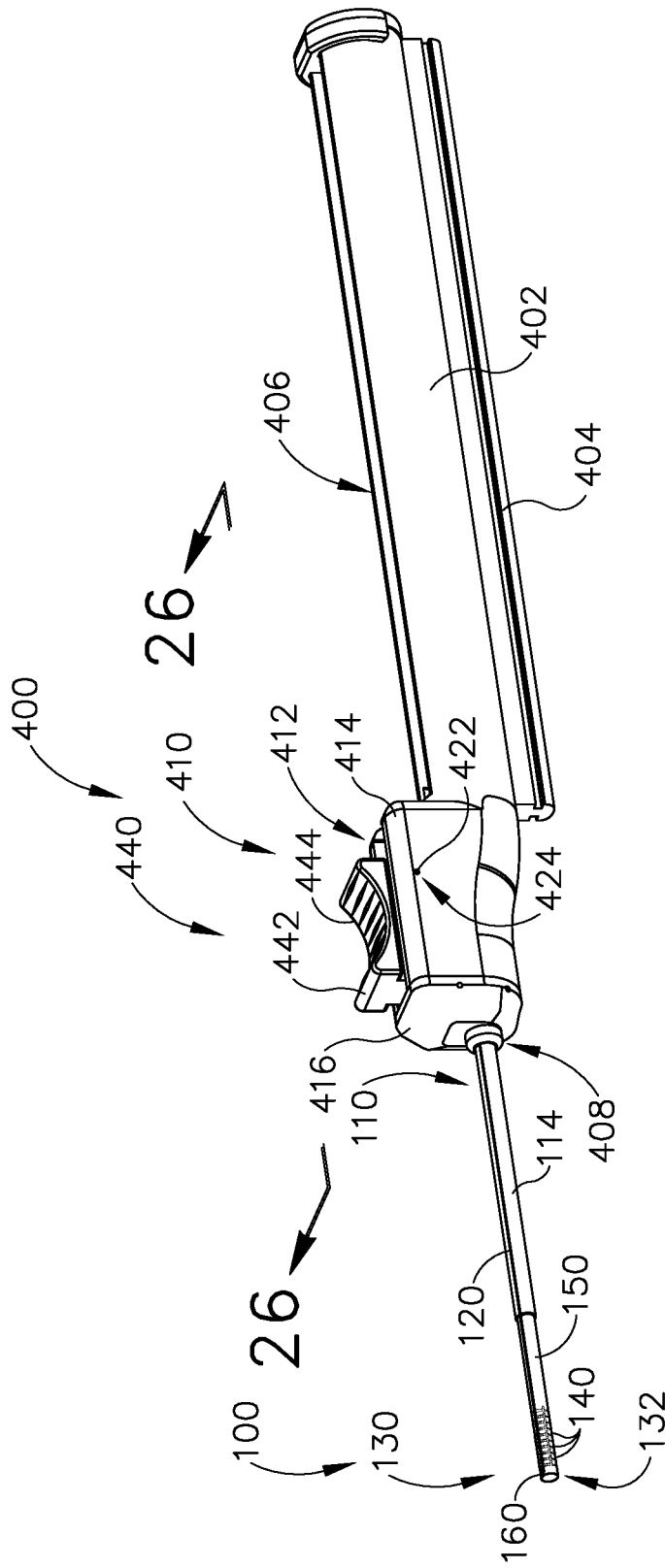
FIG. 24 depicts perspective view of the guide catheter of FIG. 8 attached to another exemplary guide catheter handle, both of which may be readily incorporated into the exemplary dilation catheter system of FIG. 1.
Figure 25:
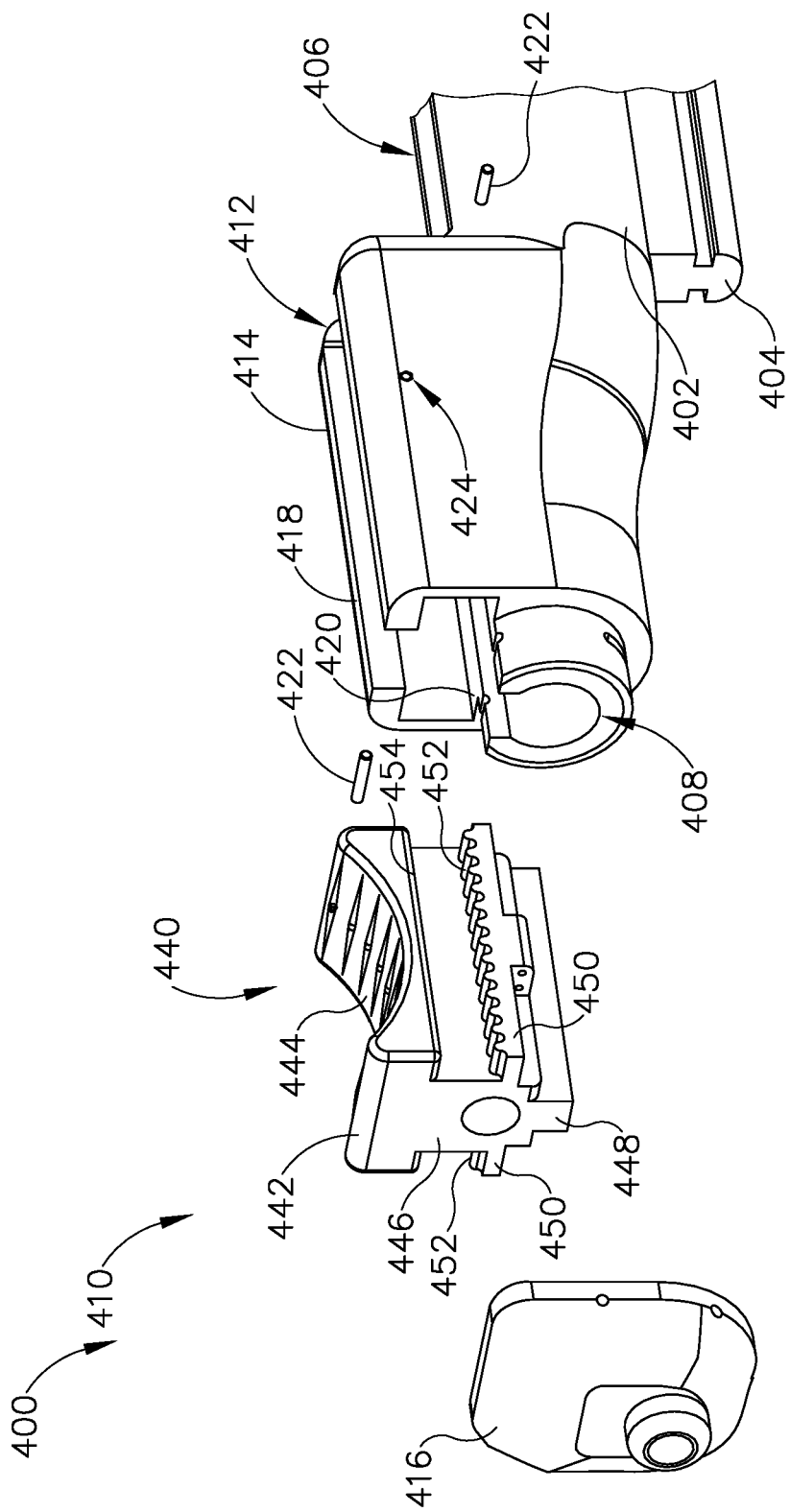
FIG. 25 depicts an exploded perspective view of the guide catheter handle of FIG. 24.

FIGS. 23A-23B show an exemplary use of guide catheter handle (300) with guide catheter (100). FIG. 23A shows translating member (350) and pull wire (120) in a distal position, corresponding with the position of articulating distal portion (130) shown in FIG. 20A. As mentioned above, pinions (344) mesh with corresponding racks (352) while rotary wheel (344) is accessible via opening (312) of articulation housing assembly (310). Therefore, if an operator desires to articulate distal articulation portion (130) of guide catheter (100) in order to suitably access a desired nasal cavity, an operator may rotate rotary wheel (342) in a first angular direction relative to articulation housing assembly (310) in order to rotate pinions (346) relative to articulation housing assembly (310) (as shown in FIG. 23B). Because racks (352) mesh with corresponding pinions (346), and because racks (352) are slidably disposed on proximally presented arms (320), rotation of pinions (346) in the first angular direction longitudinally drives racks (352) in to a proximal position (as shown in FIG. 23B) relative to proximally presented arms (320). Also, because pull wire (120) is coupled with pull wire coupler (354), translation of racks (352) in the proximal direction due to rotation of pinion (346), leads to translation of pull wire (120) in the proximal direction relative to rigid shaft (114). As best seen between FIGS. 20A-20B, proximal translation of pull wire (120) leads to articulation of articulating distal portion (130) in accordance with the teachings above.

Ball nose spring plungers (348) are coupled with first portion (314) of articulation housing assembly (310) via threaded holes (326). Ball nose spring plungers (348) are configured to abut against the side of rotary wheel (342) to provide a frictional breaking force against rotary wheel (342) to help prevent unwanted rotation of rotary wheel (342). This may help prevent unwanted actuation of translating member (150) and pull wire (120), thereby helping prevent unwanted articulation of articulating distal portion (130) in response to external forces.

If an operator desires to articulate/bend articulating distal portion (130) from the bent configuration shown in FIG. 20B to the straight configuration shown in FIG. 20A, an operator may rotate rotary wheel (342) in a second, opposite, angular direction, such that pinions (246) rotate to drive racks (352) and pull wire coupler (352) back to the distal position shown in FIG. 23A. Articulating distal portion (130) may then return to the straight configuration shown in FIG. 20A in accordance with the description above.

FIGS. 24-26D show guide catheter (100) coupled to another exemplary handle (400) such that the two may be readily incorporated into dilation catheter system (10) described above, in place of guide catheter (30). Guide catheter handle (400) includes a proximal elongated body (402) defining a slide channel (406), a T-rail (404) extending along the bottom of proximal elongated body (402), an articulation housing assembly (410), and a guide catheter articulation assembly (440). As will be described in greater detail below, guide catheter articulation assembly (440) is operatively coupled with a proximal end of pull wire (120) such that guide catheter articulation assembly (440) may translate pull wire (120) relative to rigid shaft (114). As mentioned above, and as will be further described below, translation of pull wire (120) may drive articulation of articulating distal portion (130). Additionally, as will be described in greater detail below, guide catheter articulation assembly (440) may be configured to selectively lock the longitudinal location of pull wire (120) relative to rigid shaft (114) in order to maintain the articulated configuration of articulation distal portion (130).

T-rail (404) may be dimensioned to selectively couple with a handle extension, such as a handle extension comprising finger pegs to promote grasping of the instrument with a single hand. Slide channel (406) of proximal elongated body (402) may slidably couple with a first slidable body operatively coupled with dilation catheter (20) and a second slidable body operatively coupled with guide wire (50). Therefore, an operator may translate and/or rotate first body and second body relative to elongated body (402) in order to translate and/or rotate dilation catheter (20) or guide wire (50) relative to both guide catheter handle (400) and guide catheter (100). When properly coupled together in accordance with the description above, an operator may manipulate dilation catheter (20), guide wire (50), and guide catheter (100) with a single hand.

Rigid shaft (114) extends distally from and is fixed to articulation housing (410). Articulation housing (410) defines a pathway (408) configured to slidably receive dilation catheter (20), such that dilation catheter (20) may be inserted through pathway (408) in order to be inserted through the lumen defined by guide catheter (100).

Figure 26A:
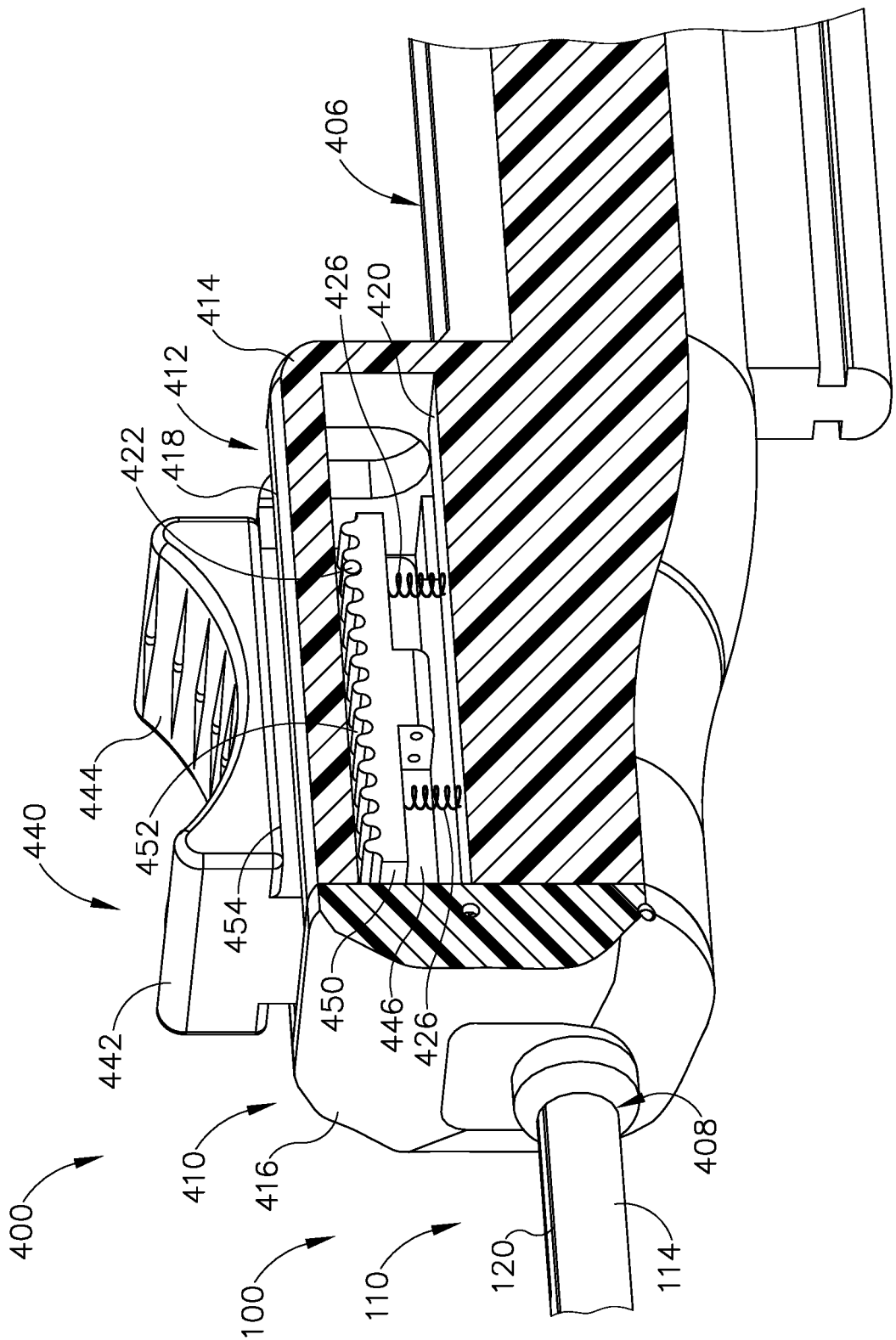
FIG. 26A depicts a cross-sectional perspective view of the guide catheter of FIG. 8 attached to the guide catheter handle of FIG. 24, where a guide catheter articulation assembly of the guide catheter handle assembly is in a first longitudinal position in a locked configuration, taken along line 26-26 of FIG. 24.
Figure 26B:
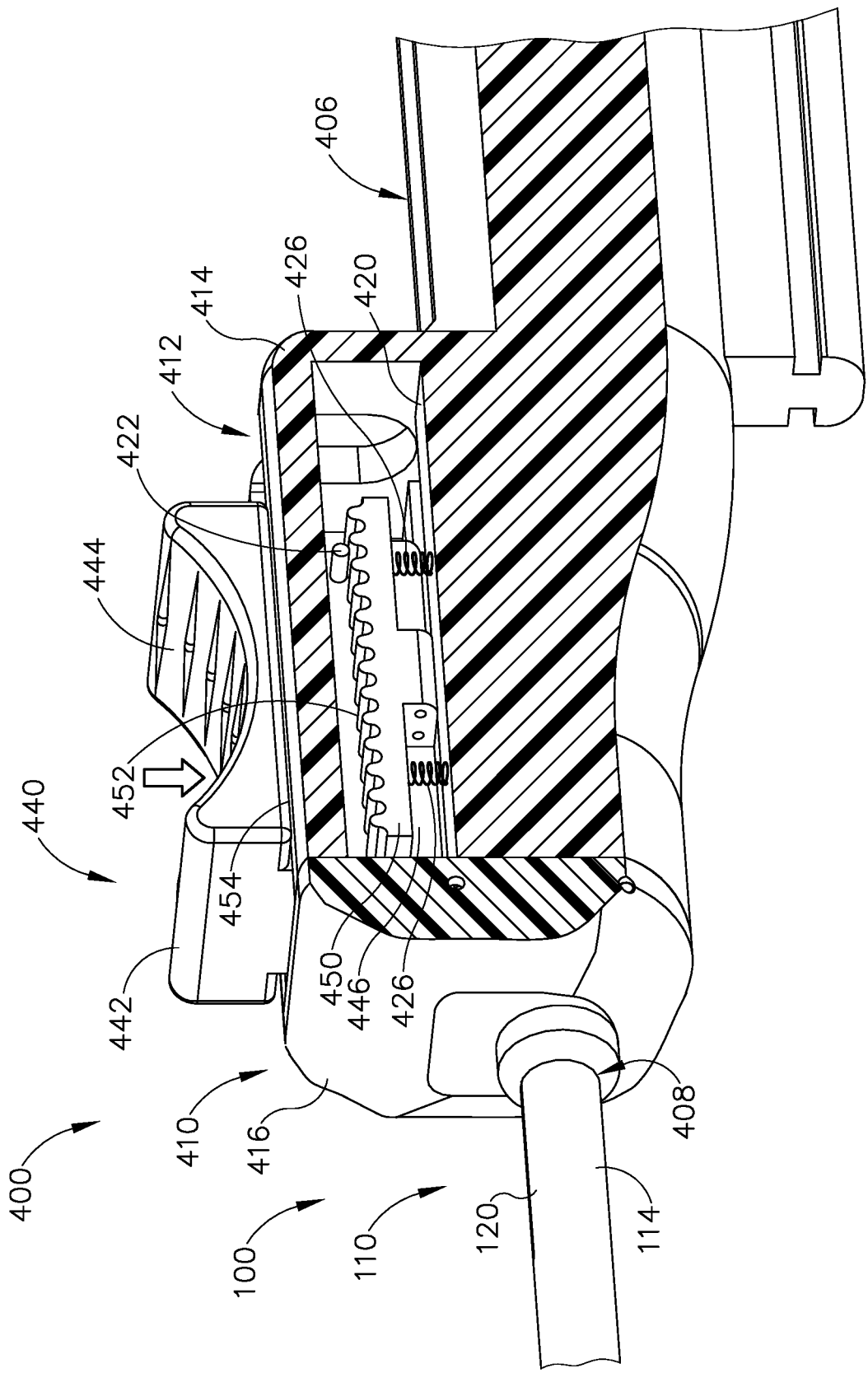
FIG. 26B depicts a cross-sectional perspective view of the guide catheter of FIG. 8 attached to the guide catheter handle of FIG. 24, where the guide catheter articulation assembly of FIG. 26A is in the first longitudinal position in an unlocked configuration, taken along line 26-26 of FIG. 24.
Figure 26C:
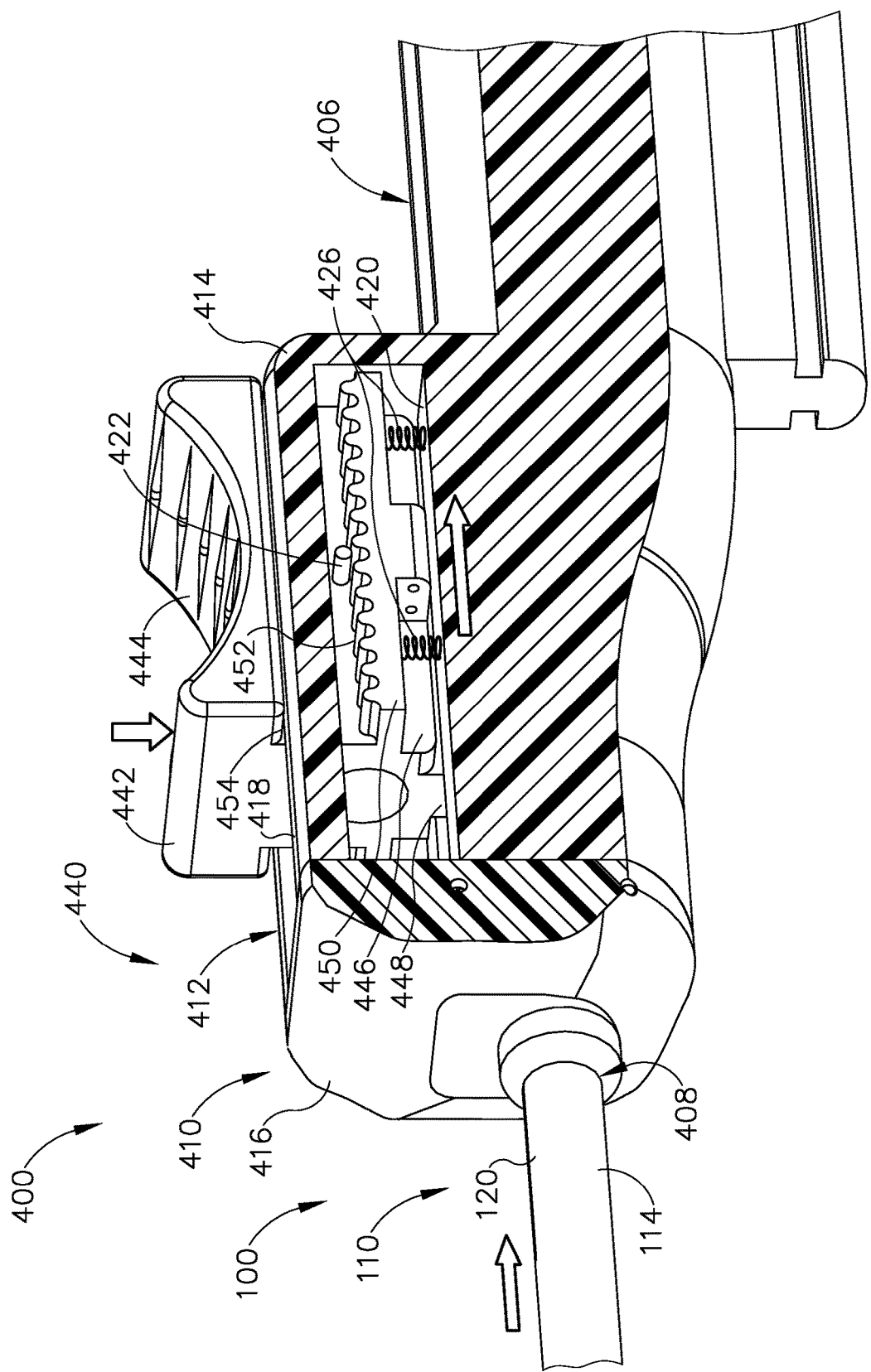
FIG. 26C depicts a cross-sectional perspective view of the guide catheter of FIG. 8 attached to the guide catheter handle of FIG. 24, where the guide catheter articulation assembly of FIG. 26A is in a second longitudinal position in the unlocked configuration, taken along line 26-26 of FIG. 24.
Figure 26D:
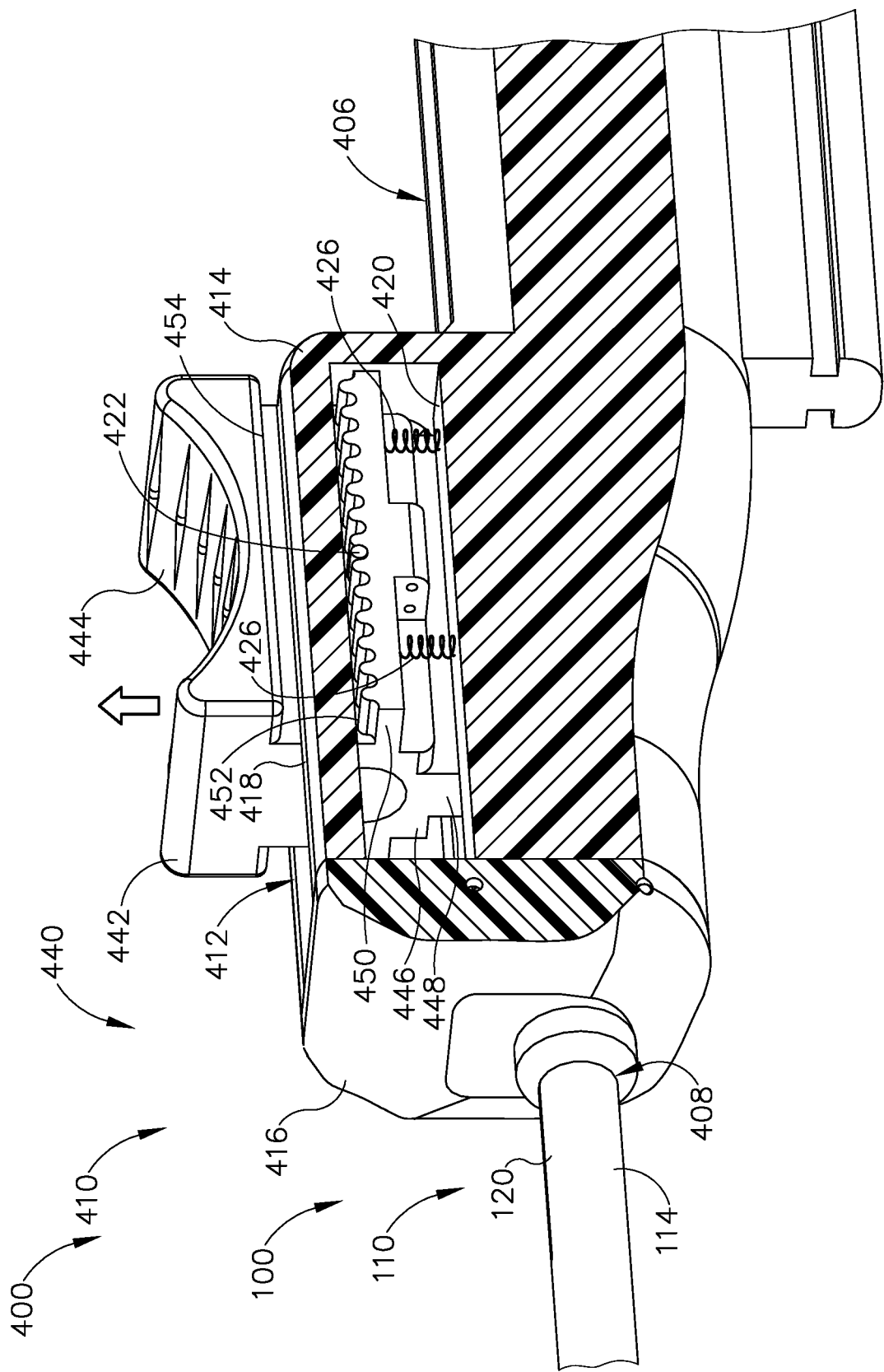
FIG. 26D depicts a cross-sectional perspective view of the guide catheter of FIG. 8 attached to the guide catheter handle of FIG. 24, where the guide catheter articulation assembly of FIG. 26A is in the second longitudinal position in the locked configuration, taken along line 26-26 of FIG. 24.

Articulation housing assembly (410) includes a first portion (414) and a second portion (416) that cooperatively define an articulation slide channel (412). Articulation slide channel (412) is dimensioned to allow guide catheter articulation assembly (440) to translate relative to articulation housing assembly (410) between a distal position (as shown in FIGS. 26A-26B) and a proximal position (as shown in FIGS. 26C-26D). As will be described in greater detail below, translation of guide catheter articulation assembly (440) is configured to longitudinally translate pull wire (120) in order to articulate/bend articulating distal portion (130) in accordance with the description above. First portion (414) also includes an exterior upwardly facing surface (418) and an interior upwardly facing surface (420). First portion (414) also defines a pin hole (424) dimensioned to receive a locking pin (422).

Guide catheter articulation assembly (440) includes a slide (442) including a finger grip body (444), a narrow portion (446), a pull wire coupler (448), and a pair of lateral protrusions (450). Lateral protrusions (450) include an upwardly presented undulating surface (452) that is configured to selectively lock against locking pin (422) as will be described in greater detail below. Finger grip body (444) includes a downwardly facing surface configured to abut against exterior upwardly facing surface (418) when guide catheter articulation assembly (440) is in an unlocked position. Pull wire coupler (448) is configured to couple with a proximal end of pull wire (120) such that translation of guide catheter articulation assembly (440) relative to articulation housing assembly (410) leads to translation of pull wire (120) relative to rigid shaft (114).

As can be seen in FIG. 26A, guide catheter articulation assembly (440) is biased into a locked position by biasing member (426) located between interior upwardly facing surface (420) and lateral protrusions (250) such that undulating surface (252) is biased into against locking pin (422). At this point, an operator cannot longitudinally translate slide (442) due to locking pin (442) being located within a valley of undulating surface (252). If an operator desires to longitudinally translate slide (442), the may push finger grip body (444) downward to overcome the upward bias of biasing members (426) to the position shown in FIG. 26B. As the position shown in FIG. 26B, slide (442) is no longer locked by undulating surface (452) interacting with locking pin (424). As can be seen, downward facing surface (454) of finger grip body (444) is in contact with exterior upwardly facing surface (418), however, this is merely optional.

With guide catheter articulation assembly (440) in the unlocked position, an operator may then actuate slide (442) proximally, which in turn also actuates pull wire (120) proximally, and therefore articulates/bends articulating distal portion (130) in accordance with the description above. An operator may then stop pressing down on slide (442) such that biasing members actuates undulating surface (452) into engagement with locking pin (422) thereby preventing unwanted longitudinal movement of slide (442) and pull wire (120), which may prevent unwanted articulation of articulating distal portion (130).

If an operator desires to straighten articulating distal portion (130), they may actuate guide catheter articulation assembly (440) in the distal direction by unlocked guide catheter articulation assembly (440) in accordance with the description above, translating guide catheter articulation assembly (440) distally, and then locking guide catheter articulation assembly (440) in accordance with the description above.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a guide catheter handle comprising an actuation assembly; (b) a guide catheter extending from an open proximal end to an open distal end, wherein the guide catheter comprises a rigid proximal portion, a bendable distal portion, and a pull wire extending from the bendable distal portion to the rigid proximal portion, wherein a proximal end of the guide wire is attached to the actuation assembly of the guide catheter handle, wherein the actuation assembly is configured to translate the pull wire relative to the rigid proximal portion to articulate the bendable distal portion.

Example 2

The apparatus of Example 1, wherein the actuation assembly includes a first bevel gear, a second bevel gear, and a translating member; wherein the translating member is fixed to the pull wire, wherein rotation of the first and second bevel gear are configured to actuate the translating member.

Example 3

The apparatus of Example 1, wherein the actuation assembly comprises a rack and pinion formation.

Example 4

The apparatus of Example 3, wherein the actuation assembly further comprises a rotary wheel configured to rotate the pinion.

Example 5

The apparatus of Example 4, wherein the actuation assembly further comprises a ball nose spring plunger configure to provide a frictional breaking force against the rotary wheel.

Example 6

The apparatus of Example 1, wherein the actuating assembly comprises an undulating surface, wherein the guide catheter handle comprises a locking pin configured to interact with the undulating surface to prevent the actuating assembly from translating the pull wire.

Example 7

The apparatus of Examples 6, wherein the undulating surface is biased to a locked position again the locking pin.

Example 8

An apparatus comprising: (a) a body; (b) an actuation assembly; and (c) a guide catheter extending distally from the body, wherein the guide catheter comprises: (i) an open proximal end, (ii) an open distal end, (iii) a rigid proximal portion, (iv) a bendable distal portion, and (v) a pull wire extending from the bendable distal portion to the rigid proximal portion, wherein a proximal end of the pull wire is coupled with the actuation assembly, wherein the actuation assembly is operable to translate the pull wire relative to the rigid proximal portion to thereby articulate the bendable distal portion.

Example 9

The apparatus of Example 8, wherein the actuation assembly comprises: (i) a first bevel gear, (ii) a second bevel gear coupled with the first bevel gear, and (iii) a translating member coupled with the second bevel gear, wherein the translating member is further coupled with the pull wire such that the bevel gears are rotatable to thereby translate the pull wire.

Example 10

The apparatus of any one or more of Examples 8 through 9, wherein the actuation assembly comprises: (i) a rack coupled with the pull wire, and (ii) a pinion coupled with the rack.

Example 11

The apparatus of Example 10, wherein the actuation assembly further comprises a rotary wheel configured to rotate the pinion.

Example 12

The apparatus of Example 11, wherein the actuation assembly further comprises a ball nose spring plunger configure to provide a frictional braking force against the rotary wheel.

Example 13

The apparatus of any one or more of Examples 3 through 12, wherein the actuating assembly comprises an undulating surface, wherein the body comprises a locking pin configured to interact with the undulating surface to prevent the actuating assembly from translating the pull wire.

Example 14

The apparatus of Example 13, wherein the undulating surface is resiliently biased to a locked position again the locking pin.

Example 15

The apparatus of any one or more of Examples 8 through 14, wherein the bendable distal portion comprises a plurality of ribs separated by gaps.

Example 16

The apparatus of Example 15, wherein each rib comprises a proximally presented protrusion and a distally presented pocket, wherein the pocket of each rib is configured to receive a corresponding protrusion of an adjacent rib of the plurality of ribs.

Example 17

The apparatus of Example 16, wherein the ribs and pockets are configured to cooperate to provide rigidity to the bendable distal portion.

Example 18

The apparatus of any one or more of Examples 15 through 17, wherein the ribs include inclined edges defining the gaps, such that the gaps are tapered.

Example 19

The apparatus of any one or more of Examples 8 through 18, wherein the body has a proximal end and a distal end, wherein the actuation assembly is located at the distal end.

Example 20

The apparatus of any one or more of Examples 8 through 19, wherein the actuation assembly includes a rotary user input feature, wherein the actuation assembly is operable to convert rotation of the rotary user input feature into translation of the pull wire.

Example 21

The apparatus of Example 20, wherein the rotary user input feature is rotatable about an axis of rotation that is transverse to a longitudinal axis of the rigid proximal portion of the guide catheter.

Example 22

The apparatus of any one or more of Examples 20 through 21, wherein the actuation assembly further includes a helical threading operable to convert rotation of the rotary user input feature into translation of the pull wire.

Example 23

The apparatus of any one or more of Examples 8 through 22, further comprising a dilation catheter slidably disposed in the guide catheter, wherein the dilation catheter includes an expandable dilator.

Example 24

The apparatus of Example 23, further comprising a guidewire slidably disposed in the dilation catheter.

Example 25

An apparatus comprising: (a) a body; (b) a guide catheter extending distally from the body, wherein the guide catheter comprises: (i) a rigid proximal portion defining a longitudinal axis, (ii) a bendable distal portion, and (iii) a translatable member extending from the bendable distal portion to the rigid proximal portion; (c) a dilation catheter slidably coupled with the guide catheter, wherein the dilation catheter includes an expandable dilator; and (d) an actuation assembly coupled with the translatable member, wherein the actuation assembly is operable to translate the translatable member to thereby deflect at least part of the bendable distal portion away from the longitudinal axis of the rigid proximal portion.

Example 26

The apparatus of Example 25, wherein the translatable member comprises a pull wire.

Example 27

A method comprising: (a) actuating a user input feature of a dilation instrument to thereby bend a bendable portion of a guide catheter of the dilation instrument, wherein the actuated user input feature translates relative to the guide catheter to thereby deflect a distal portion of the guide catheter away from a longitudinal axis defined by a proximal portion of the guide catheter; (b) inserting the distal portion of the guide catheter into a nasal cavity of a patient; (c) advancing a dilation catheter relative to the guide catheter to thereby position a dilator of the dilation catheter in an anatomical passageway of the patient; and (d) expanding the dilator to thereby dilate the anatomical passageway.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method comprising:
   actuating a user input feature of a dilation instrument to thereby bend a bendable portion of a guide catheter of the dilation instrument, wherein the actuated user input feature translates relative to the guide catheter to thereby deflect a distal portion of the guide catheter away from a longitudinal axis defined by a proximal portion of the guide catheter, wherein the bendable portion of the guide catheter comprises a series of ribs extending from a spine in a single piece, wherein each rib in the series of ribs comprises a protrusion on a first side of the rib and a pocket on a second side of the rib opposite the first side, wherein bending the bendable portion includes sliding the protrusions into adjacent pockets;
   inserting the distal portion of the guide catheter into a nasal cavity of a patient;
   translating a translatable sleeve slidably coupled with the proximal portion of the guide catheter, wherein the translatable sleeve includes a key configured to translate longitudinally within a slot, wherein the key is configured to restrict rotation of the translatable sleeve about the longitudinal axis;
   advancing a dilation catheter relative to the guide catheter to thereby position a dilator of the dilation catheter in an anatomical passageway of the patient;
   expanding the dilator to thereby dilate the anatomical passageway; and
   applying a resistance within the user input feature to thereby maintain the bend of the bendable portion.

2. The method of claim 1, wherein actuating the user input feature of the dilation instrument comprises rotating a knob to thereby deflect the distal portion of the guide catheter.

3. The method of claim 2, wherein the knob includes an axis of rotation that intersects the longitudinal axis, the method further comprising rotating the knob about the axis of rotation.

4. The method of claim 3, wherein a set of gears are meshed together with a first gear on the longitudinal axis and a second gear on the axis of rotation, the second gear being rotationally coupled to the knob such that rotating the knob about the axis of rotation further rotates the first gear about the longitudinal axis, wherein the first gear is further coupled with a traversing assembly configured to traverse along the longitudinal axis when the first gear rotates, the method further comprising traversing the traversing assembly by rotating the knob.

5. The method of claim 4, wherein the user input feature includes a pull wire, wherein the traversing assembly is connected to the pull wire connected to the distal portion of the guide catheter, wherein the pull wire is configured to translate with the traversing assembly and to cause the deflection of the distal portion of the guide catheter, the method further comprising translating the pull wire to thereby deflect the distal portion of the guide catheter.

6. The method of claim 1, wherein the distal portion of the guide catheter comprises a resilient material and returns to a non-deflected state which is in line with the longitudinal axis when tension from a pull wire is removed, the method further comprising removing tension in the pull wire to thereby return the distal portion of the guide catheter to the non-deflected state.

7. Method of claim 1, wherein the protrusions comprise angled surfaces and the pockets are angled such that bending the bendable portion of the guide catheter includes the protrusions sliding into adjacent pockets to form a predetermined articulated bend.

8. The method of claim 7, wherein the bendable portion of the guide catheter creates a flush lumen when bent into the predetermined articulated bend.

9. The method of claim 1, wherein the bendable portion of the guide catheter comprises openings between the ribs defined by angled surfaces of the ribs, wherein the openings comprise a tapered shape that is narrow near the spine and widens near the protrusions and pockets of the ribs.

10. The method of claim 9, wherein the tapered shape of the openings ends in a rounded shape along the spine.

11. The method of claim 9, wherein bending the bendable portion causes the openings between the ribs to close, and wherein adjacent angled surfaces of adjacent ribs fit together to create a flush portion of the bendable portion of the guide catheter.

12. A method for bending a distal portion of a guide catheter, the method comprising:
    actuating a user input feature on a body of a dilation instrument in a first direction;
    pulling a pull wire positioned at least partially inside of a rigid shaft in response to actuating the user input feature, the rigid shaft being rotatably coupled to the body and defining a longitudinal axis;
    deflecting a resilient spine away from the longitudinal axis and in response to pulling the pull wire, the resilient spine connecting a plurality of ribs ending in a distal rib to a rigid portion of the guide catheter, the ribs and spine defining an outermost radius of the guide catheter;
    bending the distal portion of the guide catheter into a predetermined bend, the predetermined bend promoted by the ribs comprising protrusions that slide into pockets of adjacent ribs and the ribs having angled surfaces such that the angled surfaces of adjacent ribs fit together to create a flush section of a surface of the catheter from the distal rib to the rigid portion when the catheter is bent into the predetermined bend;
    translating a translatable sleeve slidably coupled with the rigid shaft of the guide catheter, wherein the translatable sleeve includes a key configured to translate longitudinally within a slot, wherein the key is configured to restrict rotation of the translatable sleeve about the longitudinal axis;

releasing tension on the pull wire by actuating the user input feature in a second direction, wherein the first direction is opposite to the second direction; and straightening the resilient spine, the resilient spine straightening as a result of a combination of resiliency of material forming the resilient spine and the releasing tension on the pull wire.

13. The method of claim 12, wherein actuating the user input feature of the dilation instrument comprises rotating a knob to thereby deflect the distal portion of the guide catheter.

14. A method comprising:

inserting a distal portion of a guide catheter into a nasal cavity of a patient, the guide catheter including a spine, the guide catheter being bendable about the spine between a first orientation where the guide catheter is straight and a second orientation where the catheter is bent, a first and second rib extending from the spine in a continuous piece with a tapered gap between the first rib and the second rib when the catheter is in the first orientation, the first rib including a protrusion and the second rib including a pocket;

actuating a user input feature of the guide catheter to thereby bend and stop the spine of the guide catheter at a third orientation and to extend the protrusion of the first rib into the pocket of the second rib, the third orientation being between the first and second orientations, wherein the protrusion slides within the pocket and the tapered gap becomes narrowed when the guide catheter is in the third orientation;

translating a translatable sleeve slidably coupled with a proximal portion of the guide catheter, wherein the translatable sleeve includes a key configured to translate longitudinally within a slot and restrict rotation of the translatable sleeve;

after actuating the user input feature of the guide catheter, advancing a dilation catheter through a lumen of the guide catheter to thereby position a dilator of the dilation catheter in an anatomical passageway of the patient; and expanding the dilator to thereby dilate the anatomical passageway once the dilator has been positioned in the anatomical passageway of the patient.

\* \* \* \* \*